United States Patent
Härter et al.

(10) Patent No.: US 8,470,811 B2
(45) Date of Patent: Jun. 25, 2013

(54) SUBSTITUTED HETEROCYCLYLBENZYLPYRAZOLES AND USE THEREOF

(75) Inventors: Michael Härter, Leverkusen (DE); Hartmut Beck, Wuppertal (DE); Susanne Greschat, Wagenfeld (DE); Peter Ellinghaus, Melle (DE); Kerstin Berhörster, Essen (DE); Joachim Schuhmacher, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 10 days.

(21) Appl. No.: 13/103,305

(22) Filed: May 9, 2011

(65) Prior Publication Data

US 2012/0028950 A1 Feb. 2, 2012

(30) Foreign Application Priority Data

May 8, 2010 (EP) ..................... 10004855

(51) Int. Cl.
*A61K 31/4245* (2006.01)
*A61K 31/454* (2006.01)
*C07D 413/14* (2006.01)

(52) U.S. Cl.
USPC .................. 514/210.2; 514/326; 546/209

(58) Field of Classification Search
USPC ............ 514/364, 210.2, 406; 548/131, 364.1
See application file for complete search history.

(56) References Cited

FOREIGN PATENT DOCUMENTS

WO    WO 2008141731 A2 * 11/2008

* cited by examiner

*Primary Examiner* — Yong Chu

(57) ABSTRACT

The present application relates to novel substituted 1-[3-(heterocyclyl)benzyl]-1H-pyrazole derivatives, to processes for preparation thereof, to use thereof for treatment and/or prevention of diseases and to use thereof for production of medicaments for treatment and/or prevention of diseases, more particularly for treatment and/or prevention of hyperproliferative and angiogenic diseases and those diseases which arise from metabolic adaptation to hypoxic states. Such treatments can be effected in the form of monotherapy or else in combination with other medicaments or further therapeutic measures.

9 Claims, No Drawings

SUBSTITUTED HETEROCYCLYLBENZYLPYRAZOLES AND USE THEREOF

The present application relates to novel substituted 1-[3-(heterocyclyl)benzyl]-1H-pyrazole derivatives, to processes for preparation thereof, to use thereof for treatment and/or prevention of diseases and to use thereof for production of medicaments for treatment and/or prevention of diseases, more particularly for treatment and/or prevention of hyperproliferative and angiogenic diseases and those diseases which arise from metabolic adaptation to hypoxic states. Such treatments can be effected in the form of monotherapy or else in combination with other medicaments or further therapeutic measures.

Cancers are the consequence of uncontrolled cell growth of a wide variety of different tissues. In many cases the new cells penetrate into existing tissue (invasive growth), or they metastasize into remote organs. Cancers occur in a wide variety of different organs and often progress in a manner specific to the tissue. The term "cancer" as a generic term therefore describes a large group of defined diseases of different organs, tissue and cell types.

In 2002, 4.4 million people worldwide were diagnosed with tumours of the breast, intestine, ovaries, lung or prostate. In the same year, approx. 2.5 million deaths were assumed to be a consequence of these diseases (Globocan 2002 Report). In the USA alone, in 2005, more than 1.25 million new cases and more than 500 000 deaths were predicted from cancers. The majority of these new cases relate to cancers of the intestine (~100 000), lung (~170 000), breast (~210 000) and prostate (~230 000). A further increase in cancers of approx. 15% over the next 10 years is expected (American Cancer Society, Cancer Facts and Figures 2005).

Some tumours at early stages can be removed by surgical and radiotherapy measures. Metastasized tumours can generally only be treated palliatively by chemotherapeutics. The aim here is to achieve the optimum combination of an improvement in the quality of life and prolonging of life.

Chemotherapies are often composed of combinations of cytotoxic medicaments. The majority of these substances have bonding to tubulin as their mechanism of action, or they are compounds which interact with the formation and processing of nucleic acids. As of recently, these also include enzyme inhibitors which interfere with epigenetic DNA modification or cell cycle progression (e.g. histone deacetylase inhibitors, aurora kinase inhibitors). Since such therapies are toxic, there has recently been an increasing focus on targeted therapies in which specific processes in the cell are blocked without a high level of toxic stress. These especially include inhibitors of kinases which inhibit the phosphorylation of receptors and signal transmission molecules. One example thereof is imatinib, which is used very successfully for treatment of chronic myeloid leukaemia (CML) and gastrointestinal stromal tumours (GIST). Further examples are substances which block EGFR kinase and HER2, such as erlotinib, and VEGFR kinase inhibitors, such as sorafenib and sunitinib, which are used for kidney cell carcinomas, liver carcinomas and advanced stages of GIST.

With an antibody directed against VEGF, it has been possible to prolong the life expectancy of colorectal carcinoma patients. Bevacizumab inhibits the growth of blood vessels, which is an obstacle to rapid expansion of a tumour, since it requires connection to the blood vessel system for continuously functioning supply and disposal.

One stimulus for angiogenesis is hypoxia, which occurs time and again with solid tumours, since blood supply is inadequate because of the unregulated growth. If there is a lack of oxygen, cells switch their metabolism from oxidative phosphorylation to glycolysis, so as to stabilize the ATP level in the cell. This process is controlled by a transcription factor which is upregulated depending on the oxygen content in the cell. This transcription factor, called "hypoxia-induced factor" (HIF), is normally removed posttranslationally by rapid degradation and prevented from being transported into the cell nucleus. This is accomplished by the hydroxylation of two proline units in the oxygen-degradable domain (ODD) and one asparagine unit in the vicinity of the C terminus by the enzymes prolyl dehydrogenase and FIH ("factor inhibiting HIF"). After the modification of the proline units, HIF can be degraded with mediation by the Hippel-Lindau protein (part of a ubiquitin-E3-ligase complex) via the proteasome apparatus (Maxwell, Wiesener et al., 1999). In the event of oxygen deficiency, the degradation does not take place and the protein is upregulated and leads to transcription or to blockage of the transcription of numerous (more than 100) other proteins (Semenza and Wang, 1992; Wang and Semenza, 1995).

The transcription factor HIF is formed by the regulated α-subunit and a constitutively present β-subunit (ARNT, aryl hydrocarbon receptor nuclear translocator). There are three different species of the α-subunit, 1α, 2α and 3α, the latter being assumed to be a suppressor if anything (Makino, Cao et al., 2001). The HIF subunits are bHLH (basic helix loop helix) proteins which dimerize via their HLH and PAS (Per-Arnt-Sim) domains, which starts their transactivation activity (Jiang, Rue et al., 1996).

In the most important tumour entities, overexpression of the HIF1α protein is correlated with increasing blood vessel density and enhanced VEGF expression (Hirota and Semenza, 2006). At the same time, glucose metabolism is moved towards glycolysis, and the Krebs cycle is reduced in favour of the production of cell units. This also implies a change in lipid metabolism. Such changes appear to guarantee the survival of the tumours. If, on the other hand, the activity of HIF is now inhibited, the development of tumours could consequently be suppressed. This has already been observed in various experimental models (Chen, Zhao et al., 2003; Stoeltzing, McCarty et al., 2004; Li, Lin et al., 2005; Mizukami, Jo et al., 2005; Li, Shi et al., 2006). Specific inhibitors of the HIF-controlled metabolism should therefore be suitable as tumour therapeutics.

WO 2004/089303-A2 describes diaryl-substituted pyrazoles as mGluR5 modulators for treatment of psychiatric disorders. WO 2010/072352-A1 and WO 2010/085584-A1 disclose 3-phenyl-5-(1H-pyrazol-4-yl)-1,2,4-oxadiazole derivatives as sphingosine-1-phosphate agonists for treatment of autoimmune and vascular disorders.

WO 2005/030121-A2 and WO 2007/065010-A2 describe the usability of particular pyrazole derivatives for inhibition of the expression of HIF and HIF-regulated genes in tumour cells. WO 2008/141731-A2 discloses heteroaryl-substituted N-benzylpyrazoles as inhibitors of the HIF regulation pathway for treatment of cancers. However, it has been found that many of these compounds do not have sufficient inhibitory activity or else, on the basis of their pharmacokinetic properties in animal models, are expected to have such a long half-life (>48 h) in the human body that significant substance accumulation is probable after repeated once-daily administration.

It was therefore an object of the present invention to discover and provide novel compounds which firstly act as potent inhibitors of the transactivating action of the transcription factor HIF and secondly have a pharmacokinetic profile which allows repeated once-daily administration without simultaneous occurrence of clinically relevant accumulation. Such properties could also lead overall to a broadening of the clinical employability of these HIF inhibitors and more particularly facilitate the combinability thereof with other active ingredients, for example conventional tumour chemotherapeutics.

This object is achieved by the inventive compounds described hereinafter. In structural terms, this novel group of N-benzylpyrazole derivatives features a hydroxyl- or cyano-substituted heterocyclyl radical in the 3 position of the benzyl head group, which surprisingly leads to an improved profile of properties of the compounds.

The present invention relates specifically to compounds of the formula (I)

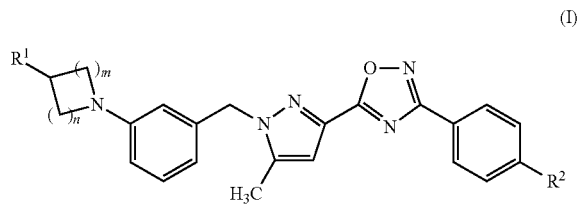

(I)

in which
m is 1 or 2,
n is 1, 2 or 3,
$R^1$ is hydroxyl or cyano,
and
$R^2$ is trifluoromethoxy, trifluoromethylsulphanyl, trifluoromethylsulphonyl, pentafluorosulphanyl or a group of the formula

in which
  * denotes the bonding site to the phenyl ring,
  $R^{3A}$ and $R^{3B}$ are each independently fluorine or methyl
  or
    are joined to one another and, together with the carbon atom to which they are bonded, form a cyclopropane-1,1-diyl, cyclobutane-1,1-diyl, cyclopentane-1,1-diyl, cyclohexane-1,1-diyl, oxetane-3,3-diyl or tetrahydro-2H-pyran-4,4-diyl ring
  and
  $R^4$ is hydrogen, fluorine, methyl, trifluoromethyl or methoxy,
and the salts, solvates and solvates of the salts thereof.

Preference is given in the context of the present invention to compounds of the formula (I) in which
m and n are each independently 1 or 2,
$R^1$ is hydroxyl or cyano,
and
$R^2$ is trifluoromethyl, trifluoromethoxy, trifluoromethylsulphanyl or a group of the formula

in which
  * denotes the bonding site to the phenyl ring,
  $R^{3A}$ and $R^{3B}$ are both methyl or are joined to one another and, together with the carbon atom to which they are bonded, form a cyclopropane-1,1-diyl, cyclobutane-1,1-diyl, oxetane-3,3-diyl or tetrahydro-2H-pyran-4,4-diyl ring
  and
  $R^4$ is hydrogen, fluorine, methyl or trifluoromethyl,
and the salts, solvates and solvates of the salts thereof.

Particular preference is given in the context of the present invention to compounds of the formula (I) in which
m and n are both 1 or 2,
$R^1$ is hydroxyl or cyano,
and
$R^2$ is trifluoromethoxy or a group of the formula

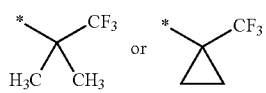

in which
  * denotes the bonding site to the phenyl ring,
and the salts, solvates and solvates of the salts thereof.

A particular embodiment of the present invention relates to compounds of the formula (I) in which
$R^1$ is hydroxyl,
and
m, n and $R^2$ are each as defined above,
and the salts, solvates and solvates of the salts thereof.

This latter embodiment corresponds to compounds of the formula (I-A)

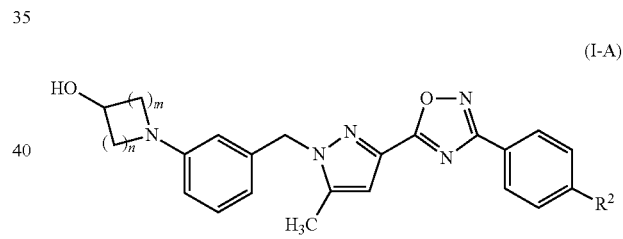

(I-A)

in which m, n and $R^2$ are each as defined above,
and the salts, solvates and solvates of the salts thereof.

In a further aspect, the present invention also relates to particular prodrugs of compounds of the formula (I-A). In general, the term "prodrugs" refers here to covalent derivatives of the compounds of the formula (I-A), which may themselves be biologically active or inactive, but are converted while present in the body, for example by a metabolic or hydrolytic route, to compounds of the formula (I-A).

The present invention accordingly further provides compounds of the formula (I-PD)

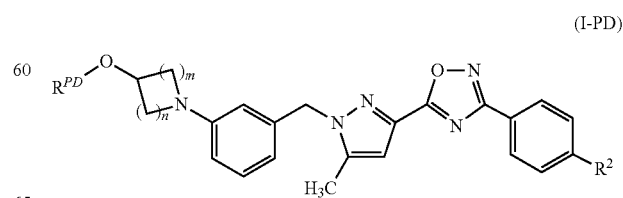

(I-PD)

in which m, n and $R^2$ are each as defined above and
$R^{PD}$ is a prodrug group of the formula

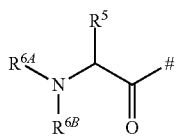

in which
# denotes the bonding site to the oxygen atom,
$R^5$ is hydrogen or $(C_1-C_4)$-alkyl,
and
$R^{6A}$ and $R^{6B}$ are each independently hydrogen or methyl,
and the salts, solvates and solvates of the salts thereof.

Preference is given in the context of the present invention to compounds of the formula (I-PD) in which
$R^{PD}$ is a prodrug group of the formula

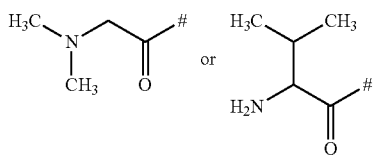

in which
# denotes the bonding site to the oxygen atom,
and the salts, solvates and solvates of the salts thereof.

The compounds of the formula (I-PD) are prodrugs of the compounds of the formula (I-A) with a good solubility in aqueous or other physiologically compatible media; they additionally offer the possibility of salt formation with appropriate acids, which can lead to a further increase in solubility. The compounds of the formula (I-PD) and salts thereof are therefore especially suitable for intravenous administration forms or else for solid formulations with modified release characteristics. This could also open up additional therapeutic fields of use for these compounds.

Inventive compounds are thus the compounds of the formulae (I), (I-A) and (I-PD) and the salts, solvates and solvates of the salts thereof, the compounds, encompassed by the formulae (I), (I-A) and (I-PD), of the formulae specified hereinafter and the salts, solvates and solvates of the salts thereof, and the compounds encompassed by the formulae (I), (I-A) and (I-PD) and specified hereinafter as working examples and the salts, solvates and solvates of the salts thereof, to the extent that the compounds encompassed by the formulae (I), (I-A) and (I-PD) and specified hereinafter are not already salts, solvates and solvates of the salts.

Depending on their structure, the inventive compounds may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the inventive compounds may therefore in some cases also constitute a preferred embodiment of the present invention. Isotopic variants of the inventive compounds can be prepared by generally customary processes known to those skilled in the art, for example by the methods described below and the methods described in the working examples, by using corresponding isotopic modifications of the particular reagents and/or starting compounds therein.

In the context of the present invention, preferred salts are physiologically acceptable salts of the inventive compounds. Also encompassed are salts which are not themselves suitable for pharmaceutical applications but can be used, for example, for the isolation, purification or storage of the inventive compounds.

Physiologically acceptable salts of the inventive compounds include especially the acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

In the context of the invention, solvates refer to those forms of the inventive compounds which, in solid or liquid state, form a complex by coordination with solvent molecules. Hydrates are a specific form of the solvates in which the coordination is with water. Preferred solvates in the context of the present invention are hydrates.

In the context of the present invention, unless specified otherwise, the substituents are defined as follows:

In the context of the invention, $(C_1-C_4)$-alkyl is a straight-chain or branched alkyl radical having 1 to 4 carbon atoms. Preferred examples include: methyl, ethyl, n-propyl, isopropyl, n-butyl, isobutyl, sec-butyl, tert-butyl.

In the context of the present invention, all radicals which occur more than once are defined independently of one another. When the radicals in the inventive compounds are substituted, the radicals may be mono- or polysubstituted, unless specified otherwise. Substitution by one or two identical or different substituents is preferred. Particular preference is given to substitution by one substituent.

The individual radical definitions specified in the particular combinations or preferred combinations of radicals are, independently of the particular combinations of the radicals specified, also replaced as desired by radical definitions of other combinations.

Very particular preference is given to combinations of two or more of the preferred ranges mentioned above.

The present invention further provides a process for preparing the compounds of the formula (I), characterized in that a compound of the formula (II)

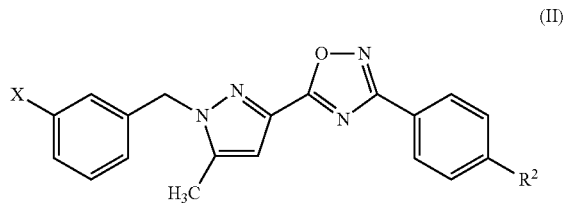

(II)

in which R² is as defined above
and
X is bromine or iodine,
in the presence of a suitable palladium catalyst and of a base, is coupled with a compound of the formula (III)

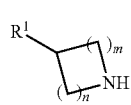

(III)

in which m, n and R¹ are each as defined above,
and the resulting compounds of the formula (I) are optionally separated into the enantiomers and/or diastereomers thereof and/or converted using the appropriate (i) solvents and/or (ii) acids to the solvates, salts and/or solvates of the salts thereof.

Suitable inert solvents for the reaction (II)+(III)→(I) are, for example, aromatic hydrocarbons such as benzene, toluene or xylene, ethers such as diethyl ether, diisopropyl ether, methyl tert-butyl ether, 1,2-dimethoxyethane, bis(2-methoxyethyl) ether, tetrahydrofuran or 1,4-dioxane, or dipolar aprotic solvents such as acetonitrile, N,N-dimethylformamide (DMF), N,N-dimethylacetamide (DMA), dimethyl sulphoxide (DMSO), N,N'-dimethylpropyleneurea (DMPU), N-methylpyrrolidinone (NMP) or pyridine. It is equally possible to use mixtures of these solvents. Preference is given to using 1,2-dimethoxyethane, tetrahydrofuran, N,N-dimethylformamide or toluene.

The coupling reaction (II)+(III)→(I) is performed with the aid of a transition metal catalyst. Especially suitable for this purpose are palladium(0) catalysts, for example bis(dibenzylideneacetone)palladium(0), tris(dibenzylideneacetone)dipalladium(0) or tetrakis(triphenylphosphino)palladium(0), optionally in combination with additional phosphine ligands such as 2-dicyclohexylphosphino-2'-(N,N-dimethylamino) biphenyl, 2-dicyclohexylphosphino-2',4',6'-triisopropylbiphenyl (X-Phos) or 4,5-bis(diphenylphosphino)-9,9-dimethylxanthene (Xantphos) [cf., for example, J. Hassan et al., Chem. Rev. 102, 1359-1469 (2002)]. Preference is given to using tris(dibenzylideneacetone)dipalladium(0) in conjunction with 2-dicyclohexylphosphino-2',4',6'-triisopropylbiphenyl (X-Phos).

The coupling is generally performed with addition of a base. Especially suitable for this purpose are alkali metal carbonates, hydrogencarbonates, phosphates, hydrogenphosphates or tert-butoxides, such as sodium carbonate, potassium carbonate, caesium carbonate, sodium hydrogencarbonate, potassium hydrogencarbonate, tripotassium phosphate, disodium hydrogenphosphate, dipotassium hydrogenphosphate, sodium tert-butoxide or potassium tert-butoxide. Preference is given to using caesium carbonate or sodium tert-butoxide.

The reaction (II)+(III)→(I) is effected generally at standard pressure within a temperature range from +50° C. to +200° C., preferably at +100° C. to +150° C. However, performance at reduced or elevated pressure (e.g. from 0.5 to 5 bar) is also possible. It may be helpful to undertake the conversion with simultaneous microwave irradiation.

In the case that the R¹ radical is hydroxyl, it may be advantageous in the above-described coupling reaction (II)+(III)→(I) to temporarily keep this hydroxyl group protected. For this purpose, preference is given to using silyl ether derivatives of the compound (III), for example corresponding trimethylsilyl, triisopropylsilyl, tert-butyldimethylsilyl or tert-butyl (diphenyl)silyl ether, which are readily obtainable from the compounds (III) by known processes. On completion of coupling, these protecting groups can then be detached again by customary methods, for example by treatment with tetra-n-butylammonium fluoride.

The compounds of the formula (II) themselves can be prepared by first condensing an N'-hydroxyamidine of the formula (IV)

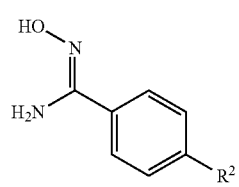

(IV)

in which R² is as defined above
with a pyrazolecarboxylic acid of the formula (V)

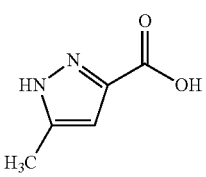

(V)

to give a 1,2,4-oxadiazole derivative of the formula (VI)

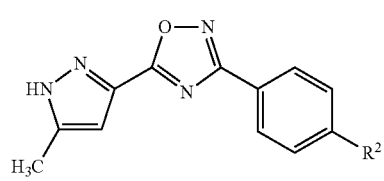

(VI)

in which R² is as defined above and then reacting the compound (VI) in the presence of a base with a compound of the formula (VII)

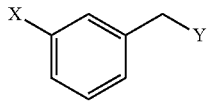
(VII)

in which X is as defined above
and
Y is a leaving group, for example chlorine, bromine, iodine, mesylate, triflate or tosylate.

The condensation reaction (IV)+(V)→(VI) is preferably performed with the aid of a carbodiimide such as N'-(3-dimethylaminopropyl)-N-ethylcarbodiimide (EDC), in conjunction with 1-hydroxy-1H-benzotriazole (HOBt) as an active ester component, or with the aid of a phosgene derivative such as 1,1'-carbonyldiimidazole (CDI) in a high-boiling dipolar aprotic solvent, for example N,N-dimethylformamide or dimethyl sulphoxide.

The initial coupling step in this reaction is effected generally within a temperature range from 0° C. to +50° C.; the cyclization to give the 1,2,4-oxadiazole is then accomplished by subsequently heating the reaction mixture to temperatures of +100° C. to +150° C. The reaction can be performed at standard, elevated or reduced pressure (e.g. from 0.5 to 5 bar); in general, standard pressure is employed.

Inert solvents for the process step (VI)+(VII)→(II) are, for example, halohydrocarbons such as dichloromethane, trichloromethane, tetrachloromethane, trichloroethylene or chlorobenzene, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane, cyclohexane or mineral oil fractions, or dipolar aprotic solvents such as acetone, methyl ethyl ketone, ethyl acetate, acetonitrile, N,N-dimethylformamide (DMF), N,N-dimethylacetamide (DMA), dimethyl sulphoxide (DMSO), N,N'-dimethylpropyleneurea (DMPU), N-methylpyrrolidinone (NMP) or pyridine. It is equally possible to use mixtures of the solvents mentioned. Preference is given to using tetrahydrofuran or 1,4-dioxane.

Suitable bases for the reaction (VI)+(VII)→(II) are customary inorganic or organic bases. These preferably include alkali metal hydroxides, for example lithium, sodium or potassium hydroxide, alkali metal alkoxides such as sodium or potassium methoxide, sodium or potassium ethoxide or sodium or potassium tert-butoxide, alkali metal hydrides such as sodium or potassium hydride, or amides such as sodium amide, lithium or potassium bis(trimethylsilyl)amide or lithium diisopropylamide. Preference is given to using potassium tert-butoxide. The addition of an alkylation catalyst, for example lithium bromide, sodium iodide, tetra-n-butylammonium bromide or benzyltriethylammonium chloride, may be advantageous.

The reaction is effected generally within a temperature range from −20° C. to +100° C., preferably at 0° C. to +60° C. The reaction can be performed at standard, elevated or reduced pressure (for example in the range from 0.5 to 5 bar); in general, standard pressure is employed.

The present invention further provides a process for preparing the compounds of the formula (I-PD), characterized in that a compound of the formula (I-A)

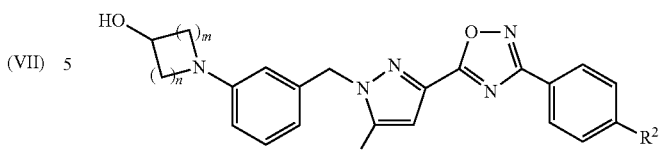
(I-A)

in which m, n and R² are each as defined above
is esterified by customary methods with a compound of the formula (VIII)

$R^{PD}$—OH (VIII)

or an activated form of this compound in which $R^{PD}$ is as defined above,
and the resulting compounds of the formula (I-PD) are optionally separated into the enantiomers and/or diastereomers thereof and/or converted using the appropriate (i) solvents and/or (ii) acids to the solvates, salts and/or solvates of the salts thereof.

Activated forms of the compound (VIII) which are suitable for the introduction of the prodrug group $R^{PD}$ are, for example, corresponding chlorides or anhydrides, including mixed anhydrides, or else particular ester or amide derivatives. A free amino group present in the $R^{PD}$ radical is appropriately present here in temporarily protected form and is then released again at the end of the esterification reaction by familiar methods. Such protection used is preferably in the form of the tert-butoxycarbonyl group, which can be detached by treatment with a strong acid, such as hydrogen chloride or trifluoroacetic acid [cf., for example, M. Bodanszky and A. Bodanszky, *The Practice of Peptide Synthesis*, Springer-Verlag, Berlin, 1984; M. Bodanszky, *Principles of Peptide Synthesis*, Springer-Verlag, Berlin, 1993; T. W. Greene and P. G. M. Wuts, *Protective Groups in Organic Synthesis*, Wiley, New York, 1999].

The compounds of the formula (I-A) themselves are obtainable via the above-described coupling reaction (II)+(III)→(I).

The compounds of the formulae (III), (IV), (V), (VII) and (VIII) are commercially available or described as such in the literature, or they can be prepared in a way obvious to the person skilled in the art, in analogy to methods published in the literature. Numerous detailed methods and literature information for preparation of the starting materials can also be found in the experimental part, in the section for preparation of the starting compounds and intermediates.

The preparation of the inventive compounds can be illustrated by the following reaction schemes:

Scheme 1

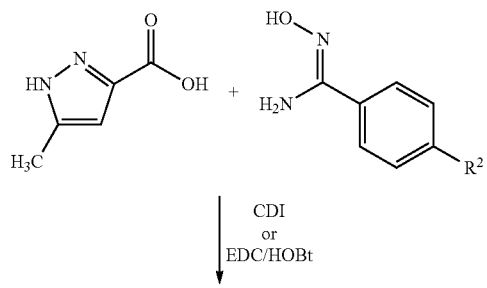

11
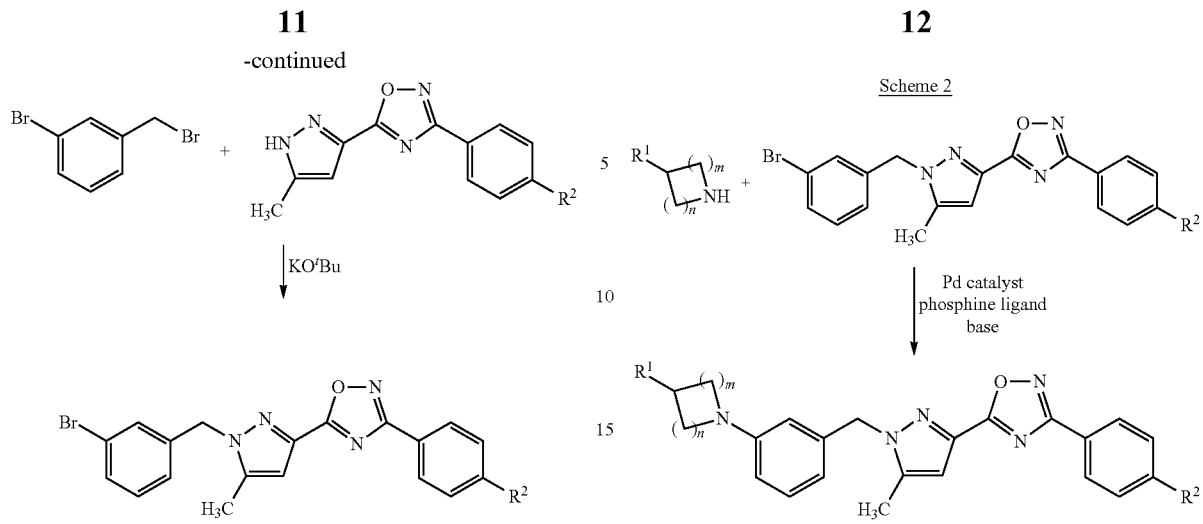
12
Scheme 2
Scheme 3
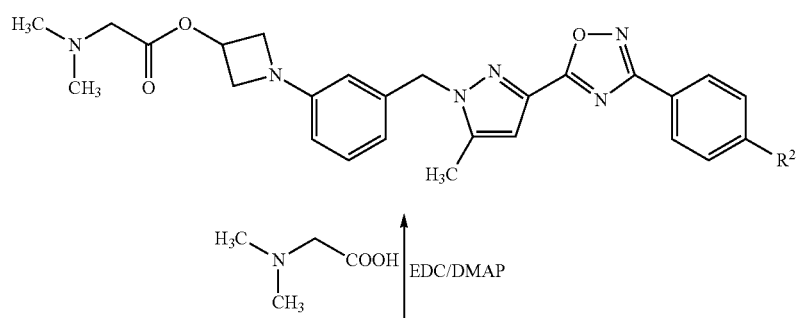
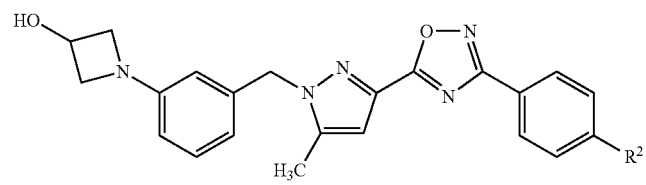
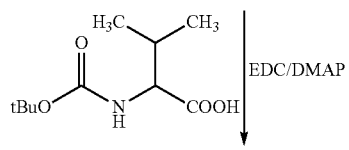
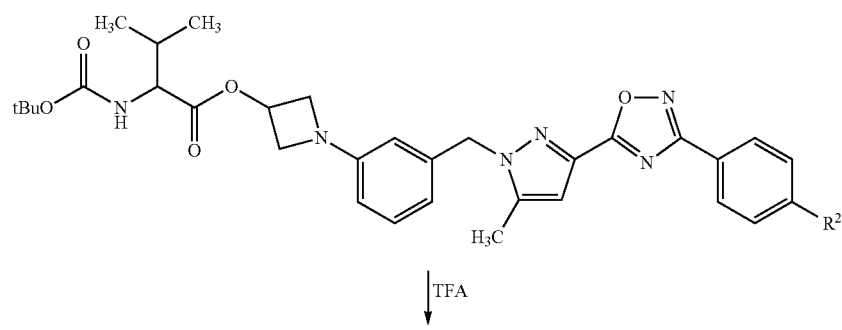

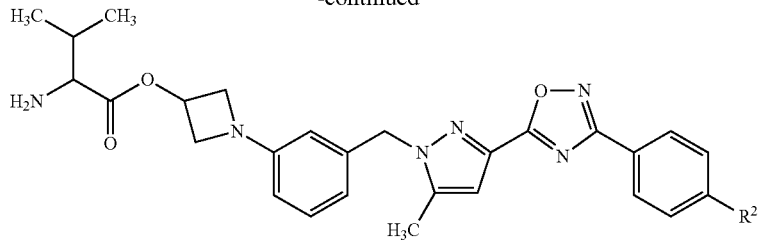

The inventive compounds have valuable pharmacological properties and can be used for prevention and treatment of diseases in humans and animals.

The inventive compounds are highly potent inhibitors of the HIF regulation pathway. In addition, the inventive compounds have advantageous pharmacokinetic properties with regard to the distribution volume thereof and/or the clearance thereof, and the half-life derived therefrom, which makes them suitable for repeated once-daily administration.

On the basis of their profile of action, the inventive compounds are especially suitable for treatment of hyperproliferative diseases in humans and in mammals in general. The compounds can inhibit, block, reduce or lower cell proliferation and cell division, and secondly increase apoptosis.

The hyperproliferative diseases which can be treated using the inventive compounds include psoriasis, keloids, formation of scars and other proliferative diseases of the skin, benign diseases, such as benign prostate hyperplasia (BPH), and especially the group of tumour diseases. In the context of the present invention, these are understood to mean especially the following diseases, but without any limitation thereto: mammary carcinomas and mammary tumours (ductal and lobular forms, also in situ), tumours of the respiratory tract (parvicellular and non-parvicellular carcinoma, bronchial carcinoma), cerebral tumours (e.g. of the brain stem and of the hypothalamus, astrocytoma, medulloblastoma, ependymoma and neuro-ectodermal and pineal tumours), tumours of the digestive organs (oesophagus, stomach, gall bladder, small intestine, large intestine, rectum), liver tumours (including hepatocellular carcinoma, cholangiocellular carcinoma and mixed hepatocellular and cholangiocellular carcinoma), tumours of the head and neck region (larynx, hypopharynx, nasopharynx, oropharynx, lips and oral cavity), skin tumours (squamous epithelial carcinoma, Kaposi's sarcoma, malignant melanoma, Merkel cell skin cancer and nonmelanomatous skin cancer) tumours of soft tissue (including soft tissue sarcomas, osteosarcomas, malignant fibrous histiocytomas, lymphosarcomas and rhabdomyosarcomas), tumours of the eyes (including intraocular melanoma and retinoblastoma), tumours of the endocrine and exocrine glands (e.g. thyroid and parathyroid glands, pancreas and salivary gland), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testicles in men). These also include proliferative blood diseases in solid form and as circulating blood cells, such as lymphomas, leukaemias and myeloproliferative diseases, for example acute myeloid, acute lymphoblastic, chronic lymphocytic, chronic myelogenic and hair cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-described diseases in humans can also occur with a comparable aetiology in other mammals and can be treated there with the compounds of the present invention.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The inventive compounds act as modulators of the HIF regulation pathway and are therefore also suitable for treatment of diseases associated with a harmful expression of the HIF transcription factor. This applies especially to the transcription factors HIF-1α and HIF-2α. The term "harmful expression of HIF" here means abnormal physiological presence of HIF protein. This can be caused by excessive synthesis of the protein (mRNA- or translation-related), by reduced degradation or by inadequate counter-regulation in the functioning of the transcription factor.

HIF-1α and HIF-2α regulate more than 100 genes. This applies to proteins which play a role in angiogenesis and are therefore directly relevant to tumours, and also those which influence glucose, amino acid and lipid metabolism, and cell migration, metastasis and DNA repair, or improve the survival of tumour cells by suppressing apoptosis. Others act more indirectly via inhibition of the immune reaction and upregulation of angiogenic factors in inflammation cells. HIF also plays an important role in stem cells, and here especially tumour stem cells, which are reported to have elevated HIF levels. The inhibition of the HIF regulation pathway by the compounds of the present invention thus also has a therapeutic influence on tumour stem cells, which do not have a high proliferation rate and therefore are affected only inadequately by cytotoxic substances (cf. Semenza, 2007; Weidemann and Johnson, 2008).

Changes in cell metabolism by HIF are not exclusive to tumours, but also occur in other hypoxic pathophysiological processes, whether chronic or transient. HIF inhibitors—such as the compounds of the present invention—are therapeutically beneficial in those contexts in which, for example, additional damage arises from adaptation of cells to hypoxic situations, since damaged cells can cause further damage if they do not function as intended. One example of this is the formation of epileptic foci in partly destroyed tissue following strokes. A similar situation is found in the case of cardiovascular diseases if ischaemic processes occur in the heart or in the brain as a consequence of thromboembolic events, inflammations, wounds, intoxications or other causes. These can lead to damage such as a locally retarded action potential, which in turn can bring about arrhythmias or chronic heart failure. In transient form, for example as a result of apnoea, there may under certain circumstances be essential hypertension, which can lead to known sequelae, for example stroke and cardiac infarction.

Inhibition of the HIF regulation pathway, as achieved by the inventive compounds, can therefore also be beneficial in the event of diseases such as heart failure, arrhythmia, myocardial infarction, apnoea-induced hypertension, pulmonary hypertension, transplant ischaemia, reperfusion damage, stroke and macular degeneration, and also for recovery of nerve function after traumatic damage or severance.

Since HIF is one of the factors which control the transition from an epithelial to a mesenchymal cell type, which is important especially for the lung and kidney, the inventive compounds can also be used to prevent or control fibroses of the lung and kidney associated with HIF.

Further diseases which can be treated using the inventive compounds are inflammatory joint diseases, such as various forms of arthritis, and inflammatory intestinal diseases, for example Crohn's disease.

Chuvash polycythaemia is mediated by HIF-2α activity during erythropoiesis, in the spleen among other organs. The inventive compounds, as inhibitors of the HIF regulation pathway, are therefore also suitable here for suppressing excessive erythrocyte formation and hence for alleviating the effects of this disease.

The compounds of the present invention can also be used for treatment of diseases associated with excessive or abnormal angiogenesis. These include diabetic retinopathy, ischaemic retinal vein occlusion and retinopathy in premature babies (cf. Aiello et al., 1994; Peer et al., 1995), age-related macular degeneration (AMD; cf. Lopez et al., 1996), neovascular glaucoma, psoriasis, retrolental fibroplasia, angiofibroma, inflammation, rheumatic arthritis (RA), restenosis, in-stent restenosis, and restenosis following vessel implantation.

Increased blood supply is additionally associated with cancerous, neoplastic tissue and leads here to accelerated tumour growth. Moreover, the growth of new blood and lymph vessels facilitates the formation of metastases and hence the spread of the tumour. New lymph and blood vessels are also harmful to allografts in immunoprivileged tissues, such as the eye, which, for example, increases susceptibility to rejection reactions. Compounds of the present invention can therefore also be used for therapy of one of the aforementioned diseases, for example by inhibition of the growth of or a reduction in the number of blood vessels. This can be achieved via inhibition of endothelial cell proliferation or other mechanisms for preventing or attenuating the formation of vessels and via a reduction of neoplastic cells by apoptosis.

In the case of obesity, HIF-1α becomes enriched in the adipose tissue, resulting in an HIF-mediated shift in the catabolism in the direction of glycolysis, such that an increased amount of glucose as an energy carrier is consumed. This leads at the same time to reduced lipid metabolism and hence to storage of lipids in the tissue. The inventive substances are therefore also suitable for treatment of HIF-1α-mediated enrichment of lipids in the tissue, especially in the case of obesity.

The present invention further provides for the use of the inventive compounds for treatment and/or prevention of disorders, especially the aforementioned disorders.

The present invention further provides for the use of the inventive compounds for production of a medicament for treatment and/or prevention of disorders, especially the aforementioned disorders.

The present invention furthermore provides the use of the inventive compounds in a method for treatment and/or prevention of disorders, especially the aforementioned disorders.

The present invention further provides a method for treatment and/or prevention of disorders, especially the aforementioned disorders, using an effective amount of at least one of the inventive compounds.

The inventive compounds can be used alone or, if required, in combination with one or more other pharmacologically active substances, provided that this combination does not lead to undesirable and unacceptable side effects. The present invention therefore further provides medicaments comprising at least one of the inventive compounds and one or more further active ingredients, especially for treatment and/or prevention of the aforementioned disorders.

For example, the compounds of the present invention can be combined with known antihyperproliferative, cytostatic or cytotoxic substances for treatment of cancers. The combination of the inventive compounds with other substances commonly used for cancer therapy or else with radiotherapy is therefore particularly appropriate, since hypoxic regions of a tumour respond only weakly to the conventional therapies mentioned, whereas the compounds of the present invention display their activity there in particular.

Examples of suitable active ingredients for combinations include:

aldesleukin, alendronic acid, alfaferone, alitertinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, regorafenib, 13-cis-retic acid, satraplatin, seocalcitol, sorafenib, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations thereof.

In a preferred embodiment, the compounds of the present invention can be combined with antihyperproliferative agents, which may be, by way of example—though this list is not exclusive:

aminoglutethimide, L-asparaginase, azathioprine, 5-azacytidine, bleomycin, busulfan, camptothecin, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenin, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

The inventive compounds can also be combined in a very promising manner with biological therapeutics, such as antibodies (for example avastin, rituxan, erbitux, herceptin) and recombinant proteins, which additively or synergistically enhance the effects of inhibition of the HIF signal pathway transmission.

Inhibitors of the HIF regulation pathway, such as the inventive compounds, can also achieve positive effects in combination with other therapies directed against angiogenesis, for example with avastin, axitinib, recentin, regorafenib, sorafenib or sunitinib. Combinations with inhibitors of the proteasome and of mTOR and antihormones and steroidal metabolic enzyme inhibitors are particularly suitable because of their favourable profile of side effects.

Generally, the following aims can be pursued with the combination of compounds of the present invention with other cytostatically or cytotoxically active agents:
- improved efficacy in slowing the growth of a tumour, in reducing its size or even in the complete elimination thereof, compared with treatment with an individual active ingredient;
- the possibility of using the chemotherapeutics used in a lower dosage than in the case of monotherapy;
- the possibility of a more tolerable therapy with fewer side effects compared with individual administration;
- the possibility of treatment of a broader spectrum of tumours;
- the achievement of a higher rate of response to the therapy;
- a longer survival time of the patient compared with present-day standard therapy.

In addition, the inventive compounds can also be used in conjunction with radiotherapy and/or surgical intervention.

The present invention further provides medicaments which comprise at least one inventive compound, typically together with one or more inert, nontoxic, pharmaceutically suitable excipients, and the use thereof for the aforementioned purposes.

The inventive compounds may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The inventive compounds can be administered in administration forms suitable for these administration routes.

Suitable administration forms for oral administration are those which work according to the prior art, which release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral and intravenous administration.

The inventive compounds can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active ingredient, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for liquid/liquid solutions are based in each case on volume.

A. Examples

| Abbreviations and acronyms: | |
|---|---|
| abs. | absolute |
| Ac | acetyl |
| aq. | aqueous |
| Ex. | Example |
| Bu | butyl |
| approx. | circa, approximately |
| CDI | 1,1'-carbonyldiimidazole |
| CI | chemical ionization (in MS) |
| d | doublet (in NMR) |
| d | day(s) |
| DAST | diethylaminosulphur trifluoride |
| TLC | thin layer chromatography |
| DCI | direct chemical ionization (in MS) |
| dd | doublet of doublets (in NMR) |
| DMAP | 4-N,N-dimethylaminopyridine |
| DME | 1,2-dimethoxyethane |
| DMF | N,N-dimethylformamide |
| DMSO | dimethyl sulphoxide |
| dt | doublet of triplets (in NMR) |
| EDC | N'-(3-dimethylaminopropyl)-N-ethylcarbodiimide hydrochloride |
| ee | enantiomeric excess |
| EI | electron impact ionization (in MS) |
| eq. | equivalent(s) |
| ESI | electrospray ionization (in MS) |
| Et | ethyl |
| GC | gas chromatography |
| h | hour(s) |
| HOBt | 1-hydroxy-1H-benzotriazole hydrate |
| HPLC | high-pressure high-performance liquid chromatography |
| $^i$Pr | isopropyl |
| LC-MS | liquid chromatography-coupled mass spectrometry |
| lit. | literature (reference) |
| m | multiplet (in NMR) |
| Me | methyl |
| min | minute(s) |

-continued

| Abbreviations and acronyms: | |
|---|---|
| MPLC | medium pressure liquid chromatography (over silica gel; also called "flash chromatography") |
| Ms | methanesulphonyl (mesyl) |
| MS | mass spectrometry |
| NMP | N-methyl-2-pyrrolidinone |
| NMR | nuclear magnetic resonance spectrometry |
| Pd/C | palladium on activated carbon |
| PEG | polyethylene glycol |
| Pr | propyl |
| quart | quartet (in NMR) |
| quint | quintet (in NMR) |
| $R_f$ | retention index (in TLC) |
| RT | room temperature |
| $R_t$ | retention time (in HPLC) |
| s | singlet (in NMR) |
| sept | septet (in NMR) |
| t | triplet (in NMR) |
| TBAF | tetra-n-butylammonium fluoride |
| $^t$Bu | tert-butyl |
| Tf | trifluoromethylsulphonyl (triflyl) |
| TFA | trifluoroacetic acid |
| THF | tetrahydrofuran |
| UV | ultraviolet spectrometry |
| v/v | volume to volume ratio (of a solution) |

HPLC, LC/MS and GC/MS Methods:

Method 1 (LC/MS):

MS instrument type: Micromass ZQ; HPLC instrument type: HP 1100 Series; UV DAD; column: Phenomenex Gemini 3μ, 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC/MS):

Instrument: Micromass Quattro Micro MS with HPLC Agilent Series 1100; column: Thermo Hypersil GOLD 3μ, 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 3 (LC/MS):

MS instrument type: Micromass ZQ; HPLC instrument type: Waters Alliance 2795; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A 4.01 min 90% A; flow rate: 2 ml/min; oven: 50° C.; UV detection: 210 nm.

Method 4 (LC/MS):

Instrument: Micromass Quattro Premier with Waters UPLC Acquity; column: Thermo Hypersil GOLD 1.9μ, 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; flow rate: 0.33 ml/min; oven: 50° C.; UV detection: 210 nm.

Method 5 (LC/MS):

Instrument: Micromass Quattro LCZ with HPLC Agilent Series 1100; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 6 (LC/MS):

Instrument: Waters Acquity SQD UPLC System; column: Waters Acquity UPLC HSS T3 1.8μ, 50 mm×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; flow rate: 0.40 ml/min; oven: 50° C.; UV detection: 210-400 nm.

Method 7 (LC/MS):

MS instrument type: Waters ZQ; HPLC instrument type: Agilent 1100 Series; UV DAD; column: Thermo Hypersil GOLD 3μ, 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 8 (LC/MS):

MS instrument type: Micromass ZQ; HPLC instrument type: HP 1100 Series; UV DAD; column: Phenomenex Gemini 3μ, 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min 2 ml/min/4.5 min 2 ml/min; oven: 50° C.; UV detection: 210 nm.

Method 9 (GC/MS):

Instrument: Micromass GCT, GC 6890; column: Restek RTX-35, 15 m×200 μm×0.33 μm; constant flow rate of helium: 0.88 ml/min; oven: 70° C.; inlet: 250° C.; gradient: 70° C., 30° C./min→310° C. (hold for 3 min)

Method 10 (analytical HPLC):

Instrument: HP 1100 with DAD detection; column: Kromasil 100 RP-18, 60 mm×2.1 mm, 3.5 μm; eluent A: 5 ml of perchloric acid (70%)/1 of water, eluent B: acetonitrile; gradient: 0 min 2% B→0.5 min 2% B 4.5 min 90% B→6.5 min 90% B→6.7 min 2% B→7.5 min 2% B; flow rate: 0.75 ml/min; column temperature: 30° C.; UV detection: 210 nm.

Method 11 (Preparative HPLC):

Column: Grom-Sil 120 ODS-4 HE, 10 μm, 250 mm×30 mm; eluent and gradient programme: acetonitrile/0.1% aq. formic acid 10:90 (0-3 min), acetonitrile/0.1% aq. formic acid 10:90→95:5 (3-27 min), acetonitrile/0.1% aq. formic acid 95:5 (27-34 min), acetonitrile/0.1% aq. formic acid 10:90 (34-38 min); flow rate: 50 ml/min; temperature: 22° C.; UV detection: 254 nm.

Method 12 (Preparative HPLC):

Column: Daiso C18 Bio Spring Column, 10 μm, 300 mm×100 mm; eluent and gradient programme: water/methanol 80:20 (0-6 min), water/methanol 80:20→20:80 (6-60 min), water/methanol 20:80 (60-95 min), water/methanol 10:90 (95-105 min), water/methanol 80:20 (105-113 min); flow rate: 250 ml/min; temperature: 25° C.; UV detection: 240 nm.

Method 13 (Preparative HPLC):

Column: Reprosil-Pur C18, 10 μm, 250 mm×30 mm; eluent and gradient programme: acetonitrile/0.1% aq. formic acid 10:90 (0-3 min), acetonitrile/0.1% aq. formic acid 10:90→95:5 (3-27 min), acetonitrile/0.1% aq. formic acid 95:5 (27-34 min), acetonitrile/0.1% aq. formic acid 10:90 (34-38 min); flow rate: 50 ml/min; temperature: 22° C.; UV detection: 254 nm.

Method 14 (LC/MS):

Instrument: Waters Acquity SQD UPLC System; column: Waters Acquity UPLC HSS T3 1.8μ, 30 mm×2 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; flow rate: 0.60 ml/min; oven: 50° C.; UV detection: 208-400 nm.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates:

Example 1A

5-[1-(3-Bromobenzyl)-5-methyl-1H-pyrazol-3-yl]-3-[4-(trifluoromethoxy)phenyl]-1,2,4-oxadiazole

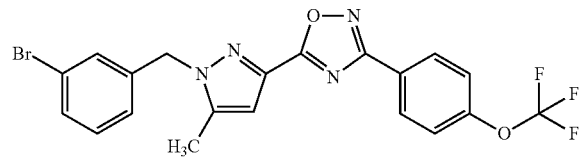

Step 1: 5-(5-Methyl-1H-pyrazol-3-yl)-3-[4-(trifluoromethoxy)phenyl]-1,2,4-oxadiazole

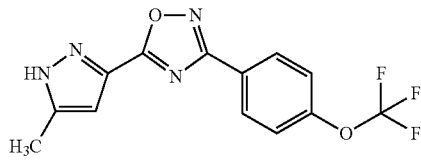 [SMILES: Cc1cc(-c2nc(-c3ccc(OC(F)(F)F)cc3)no2)n[nH]1]

To a suspension of 20.25 g (125 mmol) of 1,1'-carbonyldiimidazole in 75 ml of anhydrous DMF was added dropwise, at RT within 15 min, a solution of 15.0 g (119 mmol) of 5-methyl-1H-pyrazole-3-carboxylic acid in 75 ml of anhydrous DMF. After the mixture had been stirred at RT for 1 h 45 min, 26.19 g (119 mmol) of N'-hydroxy-4-(trifluoromethoxy)benzenecarboximide amide were added. Subsequently, the reaction mixture was heated to 110° C. for 4 h. After cooling, the majority of the solvent was removed on a rotary evaporator. 800 ml of water were added to the residue, and it was stirred for a few minutes. The undissolved product was filtered off with suction and washed with diethyl ether. The ether phase was removed from the filtrate and the aqueous phase was extracted once more with diethyl ether. 25 ml of methanol were added to the combined ether extracts, and the product which had been filtered off with suction beforehand was suspended therein. After stirring for a few minutes, the mixture was filtered off with suction again. The residue was dried under high vacuum and gave a first fraction of the title compound (8.79 g). The same amount of water was added to the filtrate, and it was extracted by shaking. After phase separation, the organic phase was washed with saturated sodium chloride solution, dried over anhydrous magnesium sulphate and finally freed of the solvent on a rotary evaporator. After the residue had been dried under high vacuum, a second fraction of the title compound was obtained in this way (24.43 g). A total of 33.32 g (90% of theory) of the title compound were thus obtained.

$^1$H NMR (400 MHz, CDCl$_3$, δ/ppm): 10.64 (broad, 1H), 8.23 (d, 2H), 7.34 (d, 2H), 6.82 (s, 1H), 2.46 (s, 3H).

LC/MS (method 4, ESIpos): R$_t$=1.28 min, m/z=311 [M+H]$^+$.

Step 2: 5-[1-(3-Bromobenzyl)-5-methyl-1H-pyrazol-3-yl]-3-[4-(trifluoromethoxy)phenyl]-1,2,4-oxadiazole

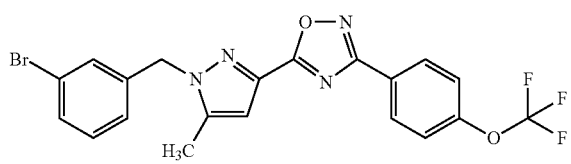 [SMILES: Cc1cc(-c2nc(-c3ccc(OC(F)(F)F)cc3)no2)nn1Cc1cccc(Br)c1]

6.58 g (58.7 mmol) of solid potassium tert-butoxide were added at RT to a solution of 14.0 g (45.1 mmol) of the compound from Example 1A/Step 1 and 13.54 g (54.2 mmol) of 3-bromobenzyl bromide in 450 ml of anhydrous dioxane. The reaction mixture was first stirred at RT for 16 h and then at 45° C. for a further 2 h, in order to complete the conversion. Subsequently, 500 ml of water were added and the mixture was extracted with approx. 300 ml each time of ethyl acetate. The combined organic extracts were washed successively with water and saturated sodium chloride solution, dried over anhydrous magnesium sulphate and finally freed of the solvent on a rotary evaporator. The resulting crude product was purified by stirring with a mixture of 525 ml of pentane and 35 ml of diisopropyl ether. After the solid had been filtered off with suction and dried, 19.08 g (84% of theory, 95% purity) of the title compound were obtained.

$^1$H NMR (400 MHz, CDCl$_3$, δ/ppm): 8.25 (d, 2H), 7.44 (d, 1H), 7.33 (d, 2H), 7.32 (s, 1H), 7.22 (t, 1H), 7.08 (d, 1H), 6.83 (s, 1H), 5.43 (s, 2H), 2.30 (s, 3H).

LC/MS (method 6, ESIpos): R$_t$=1.45 min, m/z=479/481 [M+H]$^+$.

Example 2A

5-[1-(3-Bromobenzyl)-5-methyl-1H-pyrazol-3-yl]-3-{4-[1-(trifluoromethyl)cyclopropyl]phenyl}-1,2,4-oxadiazole

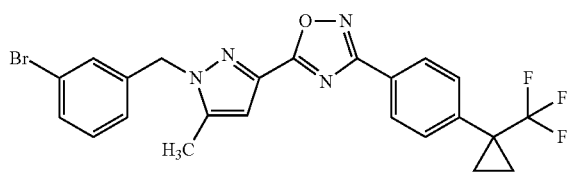 [SMILES: Cc1cc(-c2nc(-c3ccc(C4(C(F)(F)F)CC4)cc3)no2)nn1Cc1cccc(Br)c1]

Step 1: 1-Bromo-4-[1-(trifluoromethyl)cyclopropyl]benzene

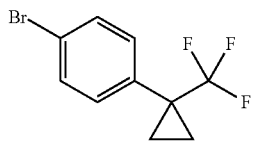 [SMILES: FC(F)(F)C1(c2ccc(Br)cc2)CC1]

First, activated zinc bromide on montmorillonite was prepared as follows: 7.0 g (31.1 mmol) of zinc bromide were initially charged in a 1 liter flask in 225 ml of methanol, and 28.2 g of K10 montmorillonite were added. Subsequently, the suspension was stirred at RT for 1 h. Then the mixture was concentrated to dryness on a rotary evaporator. The remaining fine powder was heated to bath temperature 200° C. in a sand bath under gentle vacuum (approx. 500 mbar) for 1 h and then allowed to cool under argon.

The title compound was then prepared as follows: 49.63 g (267 mmol) of 1-phenyl-1-(trifluoromethyl)cyclopropane were initially charged in 1.25 liters of pentane, and the activated zinc bromide on montmorillonite obtained above was added. Then the reaction vessel was wrapped with aluminium foil on the outside, in order to reduce the incidence of light. 137 ml (2.67 mol) of bromine were slowly added dropwise while stirring. Subsequently, the reaction mixture was stirred in the dark at RT for 16 h. Then, while cooling with ice, 1 liter of saturated aqueous sodium sulphite solution was added dropwise. The solids were filtered off with suction and washed twice with pentane. After phase separation, the filtrate was extracted twice more with 1 liter each time of pentane. The combined organic extracts were dried over anhydrous sodium sulphate, filtered and freed of the solvent on a rotary evaporator under only gentle vacuum. 77.18 g (92% purity, 100% of theory) of the title compound were obtained.

$^1$H NMR (400 MHz, CDCl$_3$, δ/ppm): 7.47 (d, 2H), 7.33 (s, 2H), 1.37-1.34 (m, 2H), 1.03-0.98 (m, 2H).

GC/MS (method 9, ESIpos): R$_t$=3.43 min, m/z=264/266 [M]$^+$.

Step 2: 4-[1-(Trifluoromethyl)cyclopropyl]benzonitrile

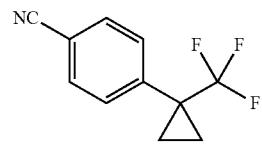 [SMILES: N#Cc1ccc(C2(C(F)(F)F)CC2)cc1]

A solution of 75.0 g (283 mmol) of the compound from Example 2A/Step 1 in a mixture of 990 ml of DMF and 10 ml of water was freed of oxygen by repeated application of a gentle vacuum and admission of argon. Then 37.87 g (322 mmol) of zinc cyanide and 32.69 g (28.3 mmol) of tetrakis(triphenylphosphine)palladium(0) were added. The reaction mixture was subsequently heated to 120° C. for 5 h. After cooling to RT, insolubles were filtered off and the residue was washed with a little DMF. The filtrate was subsequently freed of the solvent on a rotary evaporator. The resulting crude product was dissolved in 1.5 liters of ethyl acetate and the mixture was washed twice with 500 ml each time of saturated ammonium chloride solution and once with 500 ml of saturated sodium chloride solution. After drying the organic phase over anhydrous magnesium sulphate, the mixture was filtered and the filtrate was concentrated on a rotary evaporator. The oil obtained was purified by means of suction filtration through 175 g of silica gel with 40:1 cyclohexane/ethyl acetate as the eluent. After concentration of the product fractions and drying under high vacuum, 49.7 g (83% of theory) of the title compound were obtained.

$^1$H NMR (400 MHz, CDCl$_3$, δ/ppm): 7.65 (d, 2H), 7.57 (d, 2H), 1.46-1.42 (m, 2H), 1.09-1.03 (m, 2H).

GC/MS (method 9, ESIpos): R$_t$=3.79 min, m/z=211 [M]$^+$.

Step 3: N'-Hydroxy-4-[1-(trifluoromethyl)cyclopropyl]benzenecarboximide amide

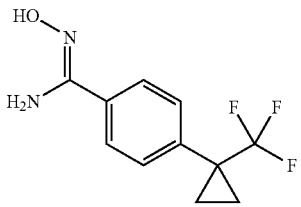 [SMILES: N/C(=N\O)c1ccc(C2(C(F)(F)F)CC2)cc1]

14.48 g (208 mmol) of hydroxylammonium chloride and 29 ml (208 mmol) of triethylamine were added to a solution of 20.0 g (94.7 mmol) of the compound from Example 2A/Step 2 in 500 ml of ethanol. The reaction mixture was heated under reflux for 2 h. Subsequently, about half of the solvent was removed on a rotary evaporator. 1.5 liters of water were added to the residue, and the resulting suspension was stirred at RT for 20 min. Then the solid was filtered off with suction, washed with a little cold water and dried under high vacuum. For further purification, it was stirred with a mixture of 120 ml of pentane and 30 ml of dichloromethane. After the solid had again been filtered off with suction and dried, 15.79 g (68% of theory) of the title compound were obtained.

$^1$H NMR (400 MHz, DMSO-$d_6$, δ/ppm): 9.68 (s, 1H), 7.67 (d, 2H), 7.46 (d, 2H), 5.83 (s, broad, 2H), 1.36-1.32 (m, 2H), 1.15-1.11 (m, 2H).

LC/MS (method 4, ESIpos): $R_t$=0.80 min, m/z=245 [M+H]$^+$.

Step 4: 5-(5-Methyl-1H-pyrazol-3-yl)-3-{4-[1-(trifluoromethyl)cyclopropyl]phenyl}-1,2,4-oxadiazole

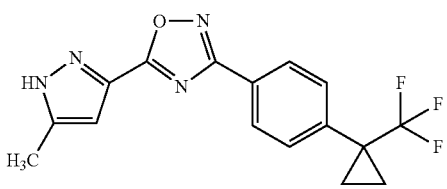 [SMILES: Cc1cc(-c2nc(-c3ccc(C4(C(F)(F)F)CC4)cc3)no2)n[nH]1]

To a suspension of 6.75 g (41.6 mmol) of 1,1'-carbonyldiimidazole in 25 ml of anhydrous DMF was added dropwise, at RT within 15 min, a solution of 5.0 g (36.6 mmol) of 5-methyl-1H-pyrazole-3-carboxylic acid in 25 ml of anhydrous DMF. After the mixture had been stirred at RT for 1 h 45 min, 9.68 g (39.6 mmol) of the compound from Example 2A/Step 3 were added. Subsequently, the reaction mixture was heated to 110° C. for 2.5 h. After cooling to RT, 800 ml of water were added gradually while stirring vigorously, as a result of which the product precipitated out. The solid was filtered off with suction and washed with a little cold water. The still-moist crude product was recrystallized from a boiling mixture of 300 ml of ethanol and 350 ml of water. 11.03 g (83% of theory) of the title compound were obtained.

$^1$H NMR (400 MHz, CDCl$_3$, δ/ppm): 11.04 (s, broad, 1H), 8.16 (d, 2H), 7.60 (d, 2H), 6.82 (s, 1H), 2.45 (s, 3H), 1.43-1.40 (m, 2H), 1.11-1.07 (m, 2H).

LC/MS (method 6, ESIpos): $R_t$=1.14 min, m/z=335 [M+H]$^+$.

Step 5: 5-[1-(3-Bromobenzyl)-5-methyl-1H-pyrazol-3-yl]-3-{4-[1-(trifluoromethyl)cyclopropyl]phenyl}-1,2,4-oxadiazole

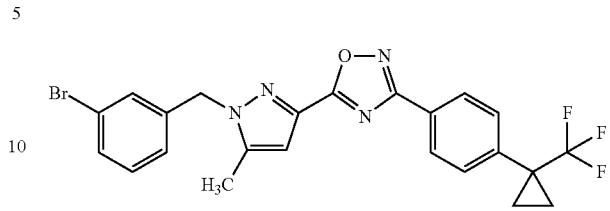

436 mg (3.89 mmol) of solid potassium tert-butoxide were added at 0° C. to a solution of 1.0 g (2.99 mmol) of the compound from Example 2A/Step 4 and 897 mg (3.59 mmol) of 3-bromobenzyl bromide in 30 ml of anhydrous dioxane. The reaction mixture was then stirred at RT for 16 h. Then approx. 200 ml of water were added and the mixture was extracted with approx. 100 ml each time of ethyl acetate. The combined organic extracts were washed successively with water and saturated sodium chloride solution, dried over anhydrous magnesium sulphate and finally freed of the solvent on a rotary evaporator. The crude product obtained was first purified by means of suction filtration through silica gel with 10:1 cyclohexane/ethyl acetate as the eluent. The product was further purified by stirring with a mixture of 50 ml of pentane and 2 ml of diethyl ether. After the solid had been filtered off with suction and dried, 1.34 g (88% of theory) of the title compound were obtained.

$^1$H NMR (400 MHz, CDCl$_3$, δ/ppm): 8.19 (d, 2H), 7.59 (d, 2H), 7.44 (d, 1H), 7.31 (s, 1H), 7.22 (t, 1H), 7.08 (d, 1H), 6.83 (s, 1H), 5.43 (s, 2H), 2.28 (s, 3H), 1.42-1.39 (m, 2H), 1.11-1.07 (m, 2H).

LC/MS (method 6, ESIpos): $R_t$=1.48 min, m/z=503/505 [M+H]$^+$.

Example 3A

5-[1-(3-Bromobenzyl)-5-methyl-1H-pyrazol-3-yl]-3-[4-(1,1,1-trifluoro-2-methylpropan-2-yl)phenyl]-1,2,4-oxadiazole

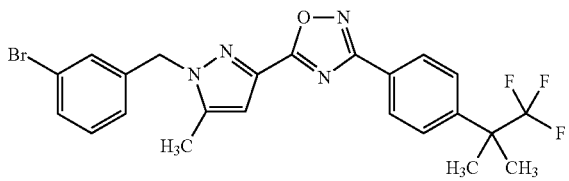 [SMILES: Cc1cc(-c2nc(-c3ccc(C(C)(C)C(F)(F)F)cc3)no2)nn1Cc1cccc(Br)c1]

Step 1: 2-(4-Bromophenyl)-1,1,1-trifluoropropan-2-ol

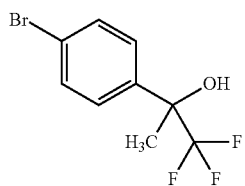

A suspension of dichloro(dimethyl)titanium in a heptane/dichloromethane mixture was first prepared as follows: 100 ml (100 mmol) of a 1 M solution of titanium tetrachloride in dichloromethane were cooled to −30° C., 100 ml (100 mmol) of a 1 M solution of dimethylzinc in heptane were added dropwise and the mixture was stirred at −30° C. for a further 30 min. Subsequently, this suspension was cooled to −40° C. and a solution of 10 g (39.5 mmol) of 1-(4-bromophenyl)-2,2,2-trifluoroethanone in 50 ml of dichloromethane was added. The mixture was stirred at −40° C. for a further 5 min, then the temperature was allowed to come to RT and the mixture was stirred at RT for a further 2 h. While cooling with ice, 50 ml of water were slowly added dropwise and then the mixture was diluted with a further 300 ml of water. The mixture was extracted twice with dichloromethane, the combined dichloromethane phases were washed once with water, dried over anhydrous magnesium sulphate and filtered, and the solvent was removed on a rotary evaporator. The residue was purified by column chromatography on silica gel (eluent: 85:15 cyclohexane/ethyl acetate). 10.5 g (100% of theory) of the title compound were obtained, which, according to $^1$H NMR, still contained residues of solvent.

$^1$H NMR (400 MHz, CDCl$_3$, δ/ppm): 7.52 (d, 2H), 7.47 (d, 2H), 1.76 (s, 3H).

LC/MS (method 1, ESIpos): R$_t$=2.27 min, m/z=268 [M+H]$^+$.

Step 2:
2-(4-Bromophenyl)-1,1,1-trifluoropropan-2-yl methanesulphonate

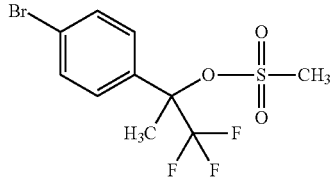 [SMILES: CC(OS(C)(=O)=O)(c1ccc(Br)cc1)C(F)(F)F]

3.12 g (78.05 mmol, 60% in mineral oil) of sodium hydride were initially charged in 45 ml of THF under argon, and a solution of 10.5 g (39.03 mmol) of the compound obtained in Example 3A/Step 1 in 20 ml of THF was added dropwise at RT. After the mixture had been stirred at RT for 1 h and at 40° C. for 30 min, a solution of 8.94 g (78.05 mmol) of methanesulphonyl chloride in 45 ml of THF was added dropwise and the reaction mixture was stirred at 40° C. for a further 60 min. Subsequently, 50 ml of water were slowly added dropwise to the mixture, which was diluted with saturated aqueous sodium hydrogencarbonate solution and extracted twice with ethyl acetate. The combined ethyl acetate phases were dried over anhydrous magnesium sulphate and filtered, and the solvent was removed on a rotary evaporator. The residue was stirred in hexane and the solid obtained was filtered off and dried under reduced pressure. 12.4 g (92% of theory) of the title compound were obtained.

$^1$H NMR (400 MHz, CDCl$_3$, δ/ppm): 7.58 (d, 2H), 7.43 (d, 2H), 3.16 (s, 3H), 2.28 (s, 3H).

LC/MS (method 2, ESIpos): R$_t$=2.32 min, m/z=364 [M+NH$_4$]$^+$.

Step 3: 1-Bromo-4-(1,1,1-trifluoro-2-methylpropan-2-yl)benzene

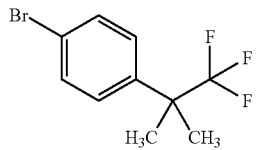

12.4 g (35.72 mmol) of the compound obtained in Example 3A/Step 2 were initially charged in 250 ml of dichloromethane and the mixture was cooled to 0° C. Then 35.7 ml (71.44 mmol) of a 2 M solution of trimethylaluminium were slowly added dropwise at 0° C. while stirring, then the mixture was allowed to come to RT and stirred at RT for a further 1.5 h. 120 ml of saturated aqueous sodium hydrogencarbonate solution were slowly added dropwise to the mixture, followed by 40 ml of saturated aqueous sodium chloride solution. The mixture was filtered through kieselguhr and the kieselguhr was washed again twice with dichloromethane. The combined dichloromethane phases were washed once with saturated aqueous sodium chloride solution and dried over anhydrous magnesium sulphate, and the solvent was removed on a rotary evaporator. 8.69 g (87% of theory) of the title compound were obtained in a purity of 95%.

$^1$H NMR (400 MHz, CDCl$_3$, δ/ppm): 7.49 (d, 2H), 7.33 (d, 2H), 1.55 (s, 6H).

GC/MS (method 9, ESIpos): R$_t$=3.48 min, m/z=266 [M]$^+$.

Step 4: 4-(1,1,1-Trifluoro-2-methylpropan-2-yl)benzenecarbonitrile

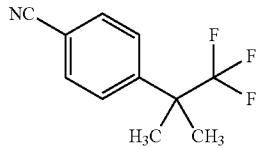

3.34 g (12.50 mmol) of the compound obtained in Example 3A/Step 3 were initially charged in 2.5 ml of degassed DMF under argon, 881 mg (7.50 mmol) of zinc cyanide and 867 mg (0.75 mmol) of tetrakis(triphenylphosphine)palladium(0) were added, and the mixture was stirred at 80° C. overnight. After cooling to RT, the reaction mixture was diluted with ethyl acetate and solid constituents were filtered off. The filtrate was washed twice with 2 N aqueous ammonia solution and once with saturated aqueous sodium chloride solution, dried over anhydrous magnesium sulphate and freed of the solvent on a rotary evaporator. The residue was purified by column chromatography on silica gel (eluent: 85:15 cyclohexane/ethyl acetate). 2.08 g (78% of theory) of the title compound were obtained.

$^1$H NMR (400 MHz, CDCl$_3$, δ/ppm): 7.68 (d, 2H), 7.62 (d, 2H), 1.60 (s, 6H).

GC/MS (method 9, ESIpos): R$_t$=3.83 min, m/z=213 [M]$^+$.

Step 5: N'-Hydroxy-4-(1,1,1-trifluoro-2-methylpropan-2-yl)benzenecarboximide amide

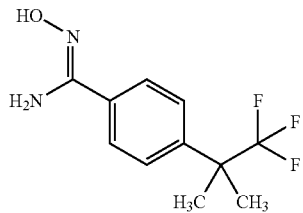 [SMILES: CC(C)(c1ccc(/C(N)=N/O)cc1)C(F)(F)F]

A mixture of 2.40 g (11.26 mmol) of the compound from Example 3A/Step 4, 1.72 g (24.77 mmol) of hydroxylamine hydrochloride and 3.45 ml (24.77 mmol) of triethylamine in 60 ml of ethanol was stirred under reflux for 1 h. After cooling to RT, the solvent was removed on a rotary evaporator. Ethyl acetate was added to the residue and the solid present was filtered off. The ethyl acetate solution was washed successively with water and saturated aqueous sodium chloride solution, dried over anhydrous magnesium sulphate and filtered. After the solvent had been removed, the oil obtained was triturated with petroleum ether. After the resulting solid had been filtered off with suction and dried under high vacuum, 2.65 g (96% of theory) of the title compound were obtained.

$^1$H NMR (400 MHz, CDCl$_3$, δ/ppm): 8.0 (s, broad, 1H), 7.62 (d, 2H), 7.52 (d, 2H), 4.88 (s, broad, 2H), 1.60 (s, 6H).

LC/MS (method 2, ESIpos): R$_t$=1.34 min, m/z=247 [M+H]$^+$.

Step 6: 5-(5-Methyl-1H-pyrazol-3-yl)-3-[4-(1,1,1-trifluoro-2-methylpropan-2-yl)phenyl]-1,2,4-oxadiazole

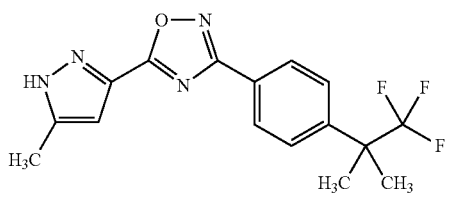 [SMILES: Cc1cc(-c2nc(-c3ccc(C(C)(C)C(F)(F)F)cc3)no2)n[nH]1]

11.6 g (60.0 mmol) of EDC, 8.13 g (60.0 mmol) of HOBt and 14.8 g (60.0 mmol) of the compound from Example 3A/Step 5 were added successively at RT to a solution of 7.57 g (60.0 mmol) of 5-methyl-1H-pyrazole-3-carboxylic acid in 300 ml of anhydrous DMF. The mixture was stirred first at RT for 2 h and then at 140° C. for 5 h. After cooling, the reaction mixture was stirred into 900 ml of ice-water. The product which precipitated out was filtered off with suction, washed with cold water and then dried under high vacuum. 14.7 g (73% of theory) of the title compound were obtained.

$^1$H NMR (400 MHz, DMSO-d$_6$, δ/ppm): 11.80 (s, broad, 1H), 8.17 (d, 2H), 7.63 (d, 2H), 6.83 (s, 1H), 2.46 (s, 3H), 1.63 (s, 6H).

LC/MS (method 4, ESIpos): R$_t$=1.34 min, m/z=337 [M+H]$^+$.

Step 7: 5-[1-(3-Bromobenzyl)-5-methyl-1H-pyrazol-3-yl]-3-[4-(1,1,1-trifluoro-2-methylpropan-2-yl)phenyl]-1,2,4-oxadiazole

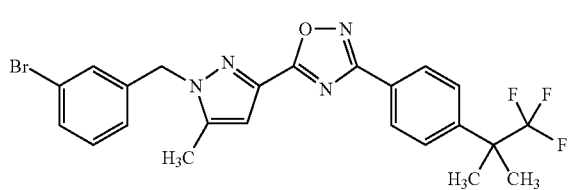 [SMILES: Cc1cc(-c2nc(-c3ccc(C(C)(C)C(F)(F)F)cc3)no2)nn1Cc1cccc(Br)c1]

Analogously to the process described in Example 2A/Step 5, 750 mg (2.23 mmol) of the compound from Example 3A/Step 6 and 669 mg (2.68 mmol) of 3-bromobenzyl bromide were used to obtain 1.02 g (84% of theory, 94% purity) of the title compound.

$^1$H NMR (400 MHz, CDCl$_3$, δ/ppm): 8.20 (d, 2H), 7.62 (d, 2H), 7.44 (d, 1H), 7.32 (s, 1H), 7.22 (t, 1H), 7.08 (d, 1H), 6.83 (s, 1H), 5.43 (s, 2H), 2.29 (s, 3H), 1.63 (s, 6H).

LC/MS (method 6, ESIpos): R$_t$=1.49 min, m/z=505/507 [M+H]$^+$.

Example 4A

5-[1-(3-Bromobenzyl)-5-methyl-1H-pyrazol-3-yl]-3-[4-(tetrahydro-2H-pyran-4-yl)phenyl]-1,2,4-oxadiazole

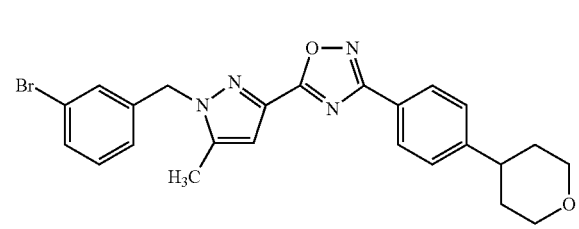 [SMILES: Cc1cc(-c2nc(-c3ccc(C4CCOCC4)cc3)no2)nn1Cc1cccc(Br)c1]

Step 1: 4-(Tetrahydro-2H-pyran-4-yl)benzonitrile

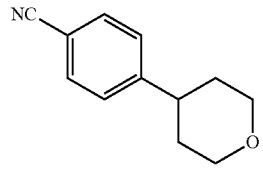

186 mg (0.594 mmol) of nickel(II) iodide, 90 mg (0.594 mmol) of trans-2-aminocyclohexanol hydrochloride and 3.63 g (19.8 mmol) of sodium hexamethyldisilazide were added to a solution of 2.91 g (19.8 mmol) of 4-cyanophenylboronic acid [M. Nishimura et al., Tetrahedron 2002, 58 (29), 5779-5788] in 20 ml of isopropanol. The suspension thus obtained was stirred at RT under an argon atmosphere for 5 min. Then 2.1 g (9.90 mmol) of 4-iodotetrahydropyran [Heuberger et al., J. Chem. Soc. 1952, 910] were added. After the reaction mixture had been stirred at a temperature of 75° C. for 15 h, it was cooled to RT and substantially freed of inorganic salts with dichloromethane by filtration through approx. 50 g of silica gel. The crude product was purified by MPLC (silica gel, eluent: dichloromethane). 986 mg (53% of theory) of the title compound were obtained.

$^1$H NMR (400 MHz, CDCl$_3$, δ/ppm): 7.60 (d, 2H), 7.32 (d, 2H), 4.12-4.07 (m, 2H), 3.56-3.50 (m, 2H), 2.87-2.79 (m, 1H), 1.86-1.73 (m, 4H).

GC/MS (method 9, ESIpos): R$_t$=5.97 min, m/z=187 [M]$^+$.

Step 2: N'-Hydroxy-4-(tetrahydro-2H-pyran-4-yl)benzenecarboximide amide

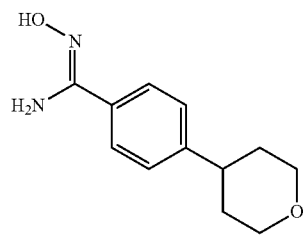 [SMILES: N/C(=N\O)c1ccc(C2CCOCC2)cc1]

480 mg (2.56 mmol) of the compound from Example 4A/Step 1, 392 mg (5.64 mmol) of hydroxylamine hydrochloride and 786 μl (5.64 mmol) of triethylamine were heated under reflux in 18 ml of ethanol for 16 h. Subsequently, the majority of the volatile components were removed on a rotary evaporator. 50 ml of water were added to the remaining residue, which was stirred at RT for a few minutes. Then the solid was filtered off with suction, washed with a little cold water and finally dried under high vacuum. 525 mg (93% of theory) of the title compound were obtained.

$^1$H NMR (400 MHz, CDCl$_3$, δ/ppm): 7.58 (d, 2H), 7.26 (d, 2H), 6.79 (broad, 1H), 4.82 (s, broad, 2H), 4.11-4.05 (m, 2H), 3.57-3.50 (m, 2H), 2.83-2.74 (m, 1H), 1.87-1.73 (m, 4H).

LC/MS (method 2, ESIpos): R$_t$=0.92 min, m/z=221 [M+H]$^+$.

Step 3: 5-(5-Methyl-1H-pyrazol-3-yl)-3-[4-(tetrahydro-2H-pyran-4-yl)phenyl]-1,2,4-oxadiazole

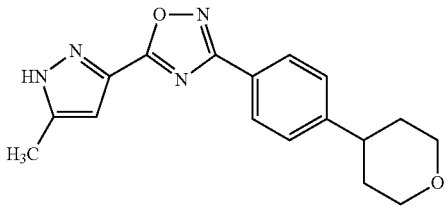 [SMILES: Cc1cc(-c2nc(-c3ccc(C4CCOCC4)cc3)no2)n[nH]1]

785 mg (4.10 mmol) of EDC, 627 mg (4.10 mmol) of HOBt and 820 mg (3.72 mmol) of the compound from Example 4A/Step 2 were added successively at RT to a solution of 469 mg (3.72 mmol) of 5-methyl-1H-pyrazole-3-carboxylic acid in 15 ml of anhydrous DMF. The mixture was stirred first at RT for 16 h and then at 140° C. for 20 min. After cooling, 100 ml of water were added to the reaction mixture, which was extracted three times with approx. 100 ml each time of ethyl acetate. The combined organic extracts were washed with saturated sodium chloride solution, dried over anhydrous magnesium sulphate and finally concentrated to dryness on a rotary evaporator. The remaining residue was used to obtain 450 mg of the title compound by extractive stirring from acetonitrile, and a further 97 mg of the title compound after purification of the mother liquor by preparative HPLC (method 13) (total yield 47% of theory).

$^1$H NMR (400 MHz, DMSO-d$_6$, δ/ppm): 13.52 (s, 1H), 8.01 (d, 2H), 7.49 (d, 2H), 6.79 (s, 1H), 3.99-3.95 (m, 2H), 3.49-3.42 (m, 2H), 2.92-2.84 (m, 1H), 2.34 (s, 3H), 1.77-1.65 (m, 4H).

LC/MS (method 6, ESIpos): R$_t$=0.98 min, m/z=311 [M+H]$^+$.

Step 4: 5-[1-(3-Bromobenzyl)-5-methyl-1H-pyrazol-3-yl]-3-[4-(tetrahydro-2H-pyran-4-yl)phenyl]-1,2,4-oxadiazole

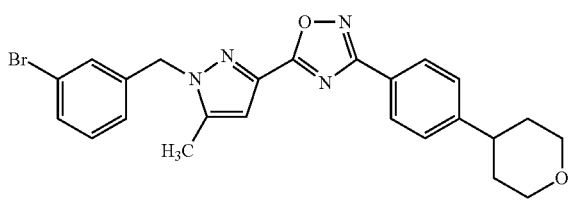 [SMILES: Cc1cc(-c2nc(-c3ccc(C4CCOCC4)cc3)no2)nn1Cc1cccc(Br)c1]

Analogously to the process described in Example 1A/Step 2, 250 mg (0.806 mmol) of the compound from Example 4A/Step 3 and 242 mg (0.967 mmol) of 3-bromobenzyl bromide were used to obtain 338 mg (87% of theory) of the title compound. The final purification of the product was effected here by extractive stirring from 10 ml of pentane/diisopropyl ether (5:1), to which a few drops of dichloromethane had been added.

$^1$H NMR (400 MHz, CDCl$_3$, δ/ppm): 8.17 (d, 2H), 7.44 (d, 1H), 7.37 (d, 2H), 7.32 (s, 1H), 7.22 (t, 1H), 7.08 (d, 1H), 6.83 (s, 1H), 5.43 (s, 2H), 4.13-4.08 (m, 2H), 2.54 (dt, 2H), 2.88-2.79 (m, 1H), 2.28 (s, 3H), 1.92-1.78 (m, 4H).

LC/MS (method 4, ESIpos): R$_t$=1.52 min, m/z=479/481 [M+H]$^+$.

Example 5A

5-[1-(3-Bromobenzyl)-5-methyl-1H-pyrazol-3-yl]-3-[4-(4-fluorotetrahydro-2H-pyran-4-yl)phenyl]-1,2,4-oxadiazole

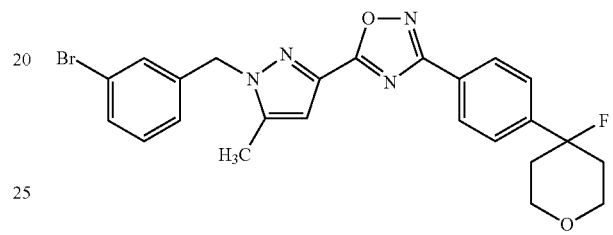

Step 1: 4-(4-Hydroxytetrahydro-2H-pyran-4-yl)benzenecarbonitrile

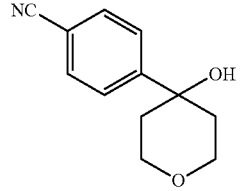 [SMILES: N#Cc1ccc(C2(O)CCOCC2)cc1]

Under inert conditions, 109 ml (218 mmol) of a 2 M solution of isopropylmagnesium chloride in diethyl ether were added dropwise at −40° C. to a solution of 50.0 g (218 mmol) of 4-iodobenzonitrile in 1000 ml of anhydrous THF. After the mixture had been stirred at the same temperature for 1.5 h, a solution of 32.8 g (327 mmol) of tetrahydro-4H-pyran-4-one in 250 ml of anhydrous THF was added. After the addition had ended, the reaction mixture was stirred first at −40° C. for 10 min, then at 0° C. for 30 min and finally at RT for 60 min. Then approx. 20 ml of saturated aqueous ammonium chloride solution were added at −20° C. Subsequently, the solvent was substantially removed on a rotary evaporator. 1000 ml of water were added to the remaining residue, which was extracted three times with approx. 500 ml each time of dichloromethane. The combined organic extracts were washed successively with water and saturated sodium chloride solution. After drying over anhydrous magnesium sulphate, the mixture was filtered and the solvent was removed on a rotary evaporator. The resulting crude product was purified by stirring with 10:1 cyclohexane/ethyl acetate. 19.3 g (43% of theory) of the title compound were obtained.

$^1$H NMR (400 MHz, DMSO-d$_6$, δ/ppm): 7.80 (d, 2H), 7.70 (d, 2H), 5.30 (s, 1H), 3.81-3.70 (m, 4H), 2.02-1.94 (m, 2H), 1.51-1.48 (m, 2H).

LC/MS (method 4, ESIpos): R$_t$=0.71 min, m/z=186 [M−H$_2$O+H]$^+$, 204 [M+H]$^+$.

Step 2: 4-(4-Fluorotetrahydro-2H-pyran-4-yl)benzenecarbonitrile

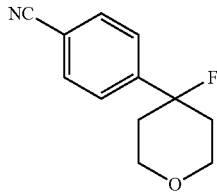 [SMILES: N#Cc1ccc(C2(F)CCOCC2)cc1]

Under inert conditions, a solution of 6.19 g (38.4 mmol) of diethylaminosulphur trifluoride (DAST) in 58 ml of dichloromethane was added dropwise at −78° C. to a suspension of 6.5 g (31.98 mmol) of the compound from Example 5A/Step 1 in 800 ml of dichloromethane. After 30 min at −78° C., the reaction mixture was warmed very rapidly to −20° C. with the aid of an ice/water bath. After approx. 30 seconds, 200 ml of 1 M sodium hydroxide solution were added and the mixture was allowed to warm to RT. After dilution with 500 ml of water, the mixture was extracted three times with approx. 200 ml each time of diethyl ether. The combined organic extracts were dried over anhydrous magnesium sulphate and, after filtration, the solvent was removed on a rotary evaporator. The crude product was purified by means of MPLC (silica gel, eluent: 10:1→5:1→2:1→1:1 cyclohexane/ethyl acetate). 3.73 g (57% of theory) of the title compound were obtained.

$^1$H NMR (400 MHz, CDCl$_3$, δ/ppm): 7.68 (d, 2H), 7.50 (d, 2H), 3.98-3.83 (m, 4H), 2.23-2.05 (m, 2H), 1.91-1.85 (m, 2H).

GC/MS (method 9, ESIpos): R$_t$=5.82 min, m/z=205 [M]$^1$.

Step 3: 4-(4-Fluorotetrahydro-2H-pyran-4-yl)-N'-hydroxybenzenecarboximide amide

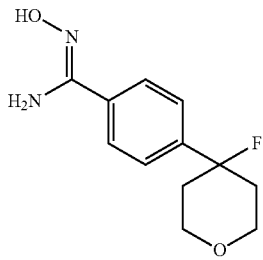 [SMILES: N/C(=N\O)c1ccc(C2(F)CCOCC2)cc1]

By the process described in Example 4A/Step 2, 3.5 g (17.05 mmol) of the compound from Example 5A/Step 2 were used to obtain 3.57 g (88% of theory) of the title compound. The reaction time in this case was 2 h.

$^1$H NMR (500 MHz, DMSO-d$_6$, δ/ppm): 9.64 (s, 1H), 7.70 (d, 2H), 7.44 (d, 2H), 5.81 (s, 2H), 3.88-3.83 (m, 2H), 3.73-3.67 (m, 2H), 2.23-2.06 (m, 2H), 1.87-1.81 (m, 2H).

LC/MS (method 4, ESIpos): R$_t$=0.40 min, m/z=239 [M+H]$^+$.

Step 4: 3-[4-(4-Fluorotetrahydro-2H-pyran-4-yl)phenyl]-5-(5-methyl-1H-pyrazol-3-yl)-1,2,4-oxadiazole

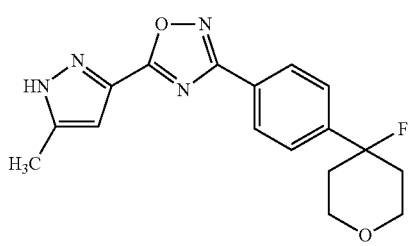 [SMILES: Cc1cc(-c2nc(-c3ccc(C4(F)CCOCC4)cc3)no2)n[nH]1]

A solution of 4.30 g (34.1 mmol) of 5-methyl-1H-pyrazole-3-carboxylic acid in 20 ml of anhydrous DMF was added dropwise at RT within approx. 15 min to a suspension of 5.81 g (35.8 mmol) of 1,1'-carbonyldiimidazole (CDI) in 25 ml of anhydrous DMF. After the mixture had been stirred at RT for 105 min, 8.12 g (34.1 mmol) of the compound from Example 5A/Step 3 were added. Subsequently, the reaction mixture was heated to 110° C. for 5 h. After cooling to RT, the mixture was stirred gradually into 800 ml of water. In the course of this, the product precipitated out. It was filtered off with suction and washed with water. Subsequently, the moist crude product was recrystallized from 430 ml of ethanol. After the solid had been filtered and dried, 8.31 g (74% of theory) of the title compound were obtained. A further fraction was obtained by concentrating the mother liquor (1.69 g with 85% purity, 13% of theory).

$^1$H NMR (400 MHz, CDCl$_3$, δ/ppm): 10.73 (broad, 1H), 8.20 (d, 2H), 7.52 (d, 2H), 6.81 (s, 1H), 4.00-3.88 (m, 4H), 2.45 (s, 3H), 2.30-2.11 (m, 2H), 1.98-1.91 (m, 2H).

LC/MS (method 1, ESIpos): R$_t$=4.24 min, m/z=329 [M+H]$^+$.

Step 5: 5-[1-(3-Bromobenzyl)-5-methyl-1H-pyrazol-3-yl]-3-[4-(4-fluorotetrahydro-2H-pyran-4-yl)phenyl]-1,2,4-oxadiazole

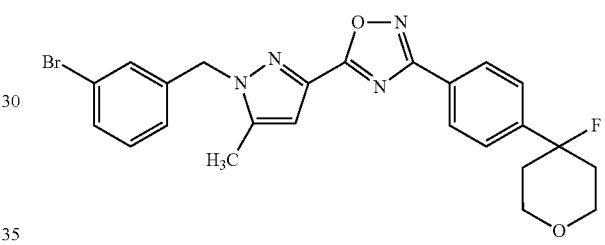

Analogously to the process described in Example 1A/Step 2, 250 mg (0.761 mmol) of the compound from Example 5A/Step 4 and 228 mg (0.914 mmol) of 3-bromobenzyl bromide were used to obtain 355 mg (94% of theory) of the title compound. It was possible here to dispense with heating the reaction mixture to 45° C. The final purification of the product was effected by extractive stirring from 10 ml of pentane/diisopropyl ether (5:1), to which a few drops of dichloromethane had been added.

$^1$H NMR (400 MHz, CDCl$_3$, δ/ppm): 8.23 (d, 2H), 7.53 (d, 2H), 7.44 (d, 1H), 7.32 (s, 1H), 7.23 (t, 1H), 7.08 (d, 1H), 6.84 (s, 1H), 5.43 (s, 2H), 4.00-3.87 (m, 4H), 2.29 (s, 3H), 2.30-2.11 (m, 2H), 1.98-1.91 (m, 2H).

LC/MS (method 4, ESIpos): R$_t$=1.52 min, m/z=497/499 [M+H]$^+$.

Example 6A

5-[1-(3-Bromobenzyl)-5-methyl-1H-pyrazol-3-yl]-3-[4-(3-fluorooxetan-3-yl)phenyl]-1,2,4-oxadiazole

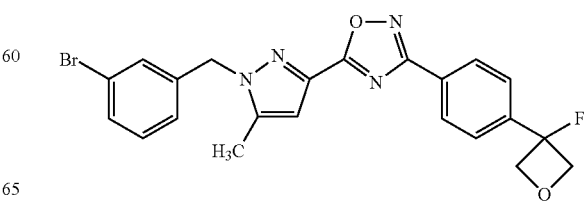

Step 1:
4-(3-Hydroxyoxetan-3-yl)benzenecarbonitrile

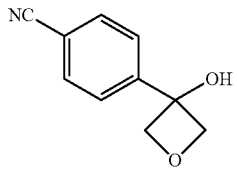 [SMILES: N#Cc1ccc(C2(O)COC2)cc1]

Under inert conditions, 11 ml (21.8 mmol) of a 2 M solution of isopropylmagnesium chloride in diethyl ether were added dropwise at −40° C. to a solution of 5.0 g (21.8 mmol) of 4-iodobenzonitrile in 100 ml of anhydrous THF. After the mixture had been stirred at the same temperature for 1.5 h, it was cooled down to −78° C. and, with the aid of a cannula, was slowly added to a solution, likewise cooled to −78° C., of 2.95 g (32.7 mmol, 80% in dichloromethane) of 3-oxooxetane [G. Wuitschik et al., *Angew. Chem. Int. Ed. Engl.* 2006, 45 (46), 7736-7739] in 100 ml of anhydrous THF. After the addition had ended, the reaction mixture was stirred first at −78° C. for 10 min, then at 0° C. for 2 h and finally at RT for 30 min. Then a few ml of saturated aqueous ammonium chloride solution were added. Subsequently, the solvent was substantially removed on a rotary evaporator. The residue obtained was diluted with 200 ml of water and extracted three times with approx. 200 ml each time of ethyl acetate. The combined organic extracts were washed successively with water and saturated sodium chloride solution. After drying over anhydrous magnesium sulphate, the mixture was filtered and the solvent was removed on a rotary evaporator. The resulting crude product was purified by crystallization from 10:1 cyclohexane/ethyl acetate. 2.42 g (63% of theory) of the title compound were obtained.

$^1$H NMR (400 MHz, DMSO-$d_6$, δ/ppm): 7.88 (d, 2H), 7.80 (d, 2H), 6.63 (s, 1H), 4.79 (d, 2H), 4.65 (d, 2H).

HPLC (method 10): $R_t$=3.09 min.

MS (DCI, $NH_3$): m/z=193 $[M+NH_4]^+$.

Step 2: 4-(3-Fluorooxetan-3-yl)benzenecarbonitrile

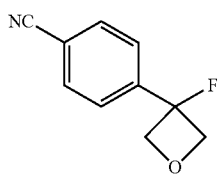 [SMILES: N#Cc1ccc(C2(F)COC2)cc1]

Analogously to the process described in Example 5A/Step 2, 600 mg (3.43 mmol) of the compound from Example 6A/Step 1 and 662 mg (4.11 mmol) of diethylaminosulphur trifluoride (DAST) were used to obtain 495 mg (82% of theory) of the title compound. For the MPLC purification, 8:1 cyclohexane/ethyl acetate was used here as the eluent.

$^1$H NMR (400 MHz, $CDCl_3$, δ/ppm): 7.76 (d, 2H), 7.73 (d, 2H), 5.15 (dd, 2H), 4.81 (dd, 2H).

LC/MS (method 2, ESIpos): $R_t$=1.59 min, m/z=178 $[M+H]^+$.

Step 3: 4-(3-Fluorooxetan-3-yl)-N'-hydroxybenzenecarboximide amide

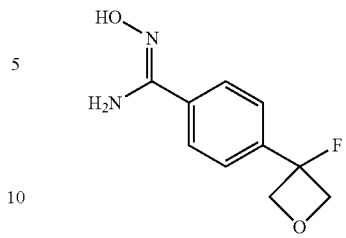

By the process described in Example 4A/Step 2, 450 mg (2.54 mmol) of the compound from Example 6A/Step 2 were used to obtain 470 mg (86% of theory) of the title compound.

$^1$H NMR (400 MHz, DMSO-$d_6$, δ/ppm): 9.71 (s, 1H), 7.77 (d, 2H), 7.54 (d, 2H), 5.87 (s, broad, 2H), 4.97 (dd, 2H), 4.91 (dd, 2H).

LC/MS (method 2, ESIpos): $R_t$=0.80 min, m/z=211 $[M+H]^+$.

Step 4: 3-[4-(3-Fluorooxetan-3-yl)phenyl]-5-(5-methyl-1H-pyrazol-3-yl)-1,2,4-oxadiazole

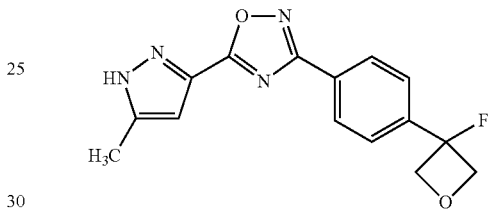

502 mg (2.62 mmol) of EDC, 401 mg (2.62 mmol) of HOBt and 500 mg (2.38 mmol) of the compound from Example 6A/Step 3 were added successively at RT to a solution of 300 mg (2.38 mmol) of 5-methyl-1H-pyrazole-3-carboxylic acid in 10 ml of anhydrous DMF. The mixture was stirred first at RT for 16 h and then at 140° C. for 45 min. After cooling, the solvent was removed on a rotary evaporator. 120 ml of water were added to the remaining residue, which was extracted three times with approx. 100 ml each time of diethyl ether. The combined organic extracts were washed with saturated sodium chloride solution, dried over anhydrous magnesium sulphate, filtered and finally concentrated on a rotary evaporator. The crude product was stirred with 5 ml of ethanol at RT for 1 h. After filtering and drying the undissolved solid under high vacuum, a first fraction of 204 mg of the title compound was obtained. The mother liquor was concentrated to dryness. Subsequently, a further fraction of 29 mg of the title compound was isolated from the residue by means of preparative HPLC (method 13). In total, 233 mg (33% of theory) of the title compound were thus obtained.

$^1$H NMR (400 MHz, $CDCl_3$, δ/ppm): 8.27 (d, 2H), 7.72 (d, 2H), 6.81 (s, 1H), 5.05 (dd, 2H), 5.01 (dd, 2H), 2.47 (s, 3H).

LC/MS (method 2, ESIpos): $R_t$=1.93 min, m/z=301 $[M+H]^+$.

Step 5: 5-[1-(3-Bromobenzyl)-5-methyl-1H-pyrazol-3-yl]-3-[4-(3-fluorooxetan-3-yl)phenyl]-1,2,4-oxadiazole

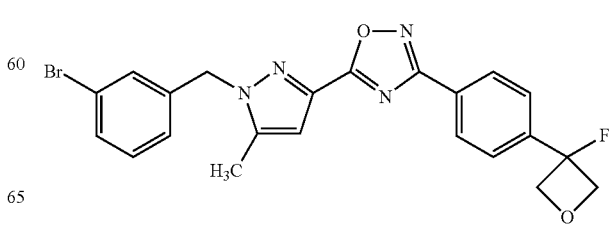

Analogously to the process described in Example 1A/Step 2, 250 mg (0.833 mmol) of the compound from Example 6A/Step 4 and 250 mg (0.999 mmol) of 3-bromobenzyl bromide were used to obtain 347 mg (89% of theory) of the title compound. It was possible here to dispense with heating the reaction mixture to 45° C. The final purification of the product was effected by extractive stirring from 10 ml of pentane/diisopropyl ether (5:1), to which a few drops of dichloromethane had been added.

$^{1}$H NMR (400 MHz, CDCl$_3$, δ/ppm): 8.30 (d, 2H), 7.72 (d, 2H), 7.45 (d, 1H), 7.33 (s, 1H), 7.22 (t, 1H), 7.09 (d, 1H), 6.85 (s, 1H), 5.43 (s, 2H), 5.04 (dd, 2H), 5.00 (dd, 2H), 2.29 (s, 3H).

LC/MS (method 4, ESIpos): R$_t$=1.46 min, m/z=469/471 [M+H]$^+$.

Example 7A

5-[1-(3-Bromobenzyl)-5-methyl-1H-pyrazol-3-yl]-3-[4-(1-methoxycyclobutyl)phenyl]-1,2,4-oxadiazole

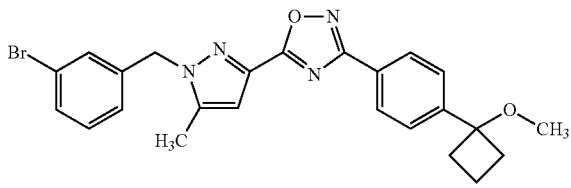 [SMILES: COC1(c2ccc(-c3noc(-c4cc(C)n(Cc5cccc(Br)c5)n4)n3)cc2)CCC1]

Step 1: 4-(1-Hydroxycyclobutyl)benzonitrile

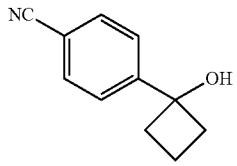 [SMILES: N#Cc1ccc(C2(O)CCC2)cc1]

Analogously to the process described in Example 5A/Step 1, 32.67 g (143 mmol) of 4-iodobenzonitrile, 75 ml (150 mmol) of 2 M isopropylmagnesium chloride solution in diethyl ether and 15.0 g (214 mmol) of cyclobutanone were used to obtain 13.31 g (78% of theory) of the title compound. The reaction time at RT in this case was 16 h, and, after the aqueous workup, the crude product was purified by means of suction filtration through 150 g of silica gel with 10:1→4:1 cyclohexane/ethyl acetate as the eluent.

$^{1}$H NMR (400 MHz, CDCl$_3$, δ/ppm): 7.67 (d, 2H), 7.62 (d, 2H), 2.58-2.51 (m, 2H), 2.44-2.37 (m, 2H), 2.23-2.04 (m, 2H), 1.83-1.72 (m, 1H).

HPLC (method 10): R$_t$=3.47 min.
MS (DCI, NH$_3$): m/z=191 [M+NH$_4$]$^+$.

Step 2: 4-(1-Methoxycyclobutyl)benzonitrile

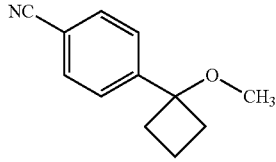

508 mg (12.7 mmol) of sodium hydride (60% suspension in mineral oil) were added at 0° C. to a solution of 2.0 g (11.5 mmol) of the compound from Example 7A/Step 1 in 40 ml of anhydrous DMF. After 1 h, 863 μl (13.9 mmol) of iodomethane were added, and the ice-water bath was removed. After stirring at RT for 16 h, the reaction mixture was poured onto 120 ml of water and extracted three times with approx. 100 ml each time of diethyl ether. The combined organic extracts were washed successively with water and saturated sodium chloride solution, dried over anhydrous magnesium sulphate, filtered and finally freed of the solvent on a rotary evaporator. The remaining residue was purified by means of suction filtration through approx. 100 g of silica gel with 20:1→4:1 cyclohexane/ethyl acetate as the eluent. 1.27 g (59% of theory) of the title compound were obtained.

$^{1}$H NMR (400 MHz, CDCl$_3$, δ/ppm): 7.68 (d, 2H), 7.54 (d, 2H), 2.95 (s, 3H), 2.46-2.32 (m, 4H), 2.03-1.93 (m, 1H), 1.76-1.63 (m, 1H).

MS (DCI, NH$_3$): m/z=205 [M+NH$_4$]$^+$.

Step 3: N'-Hydroxy-4-(1-methoxycyclobutyl)benzenecarboximide amide

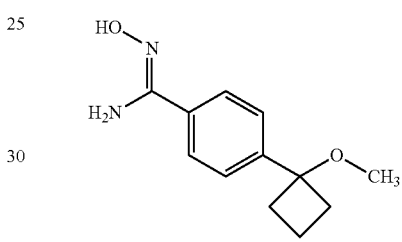

Analogously to the process described in Example 3A/Step 5, 1.10 g (5.88 mmol) of the compound from Example 7A/Step 2 and 612 mg (8.81 mmol) of hydroxylammonium chloride were used to obtain 1.28 g (93% of theory, 95% purity) of the title compound. The reaction time in this case was 16 h.

$^{1}$H NMR (400 MHz, DMSO-d$_6$, δ/ppm): 9.62 (s, 1H), 7.68 (d, 2H), 7.40 (d, 2H), 5.80 (s, broad, 2H), 2.83 (s, 3H), 2.37-2.24 (m, 4H), 1.91-1.81 (m, 1H), 1.65-1.53 (m, 1H).

HPLC (method 10): R$_t$=3.02 min.
MS (DCI, NH$_3$): m/z=221 [M+H]$^+$.

Step 4: 3-[4-(1-Methoxycyclobutyl)phenyl]-5-(5-methyl-1H-pyrazol-3-yl)-1,2,4-oxadiazole

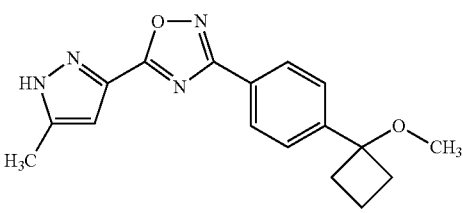

To a suspension of 491 mg (3.03 mmol) of 1,1'-carbonyldiimidazole (CDI) in 2 ml of anhydrous DMF was added dropwise, at RT within 15 min, a solution of 364 mg (2.88 mmol) of 5-methyl-1H-pyrazole-3-carboxylic acid in 2 ml of anhydrous DMF. After the mixture had been stirred at RT for 2 h, 635 mg (2.88 mmol) of the compound from Example 7A/Step 3 were added. Subsequently, the reaction mixture was heated to 110° C. for 4.5 h. After cooling to RT, the reaction mixture was stirred gradually into 60 ml of water while stirring vigorously, in the course of which the product precipitated out. The solid was filtered off with suction and washed with a little cold water. After drying under a high vacuum, 640 mg (68% of theory, 95% purity) of the title compound were obtained.

$^1$H NMR (400 MHz, CDCl$_3$, δ/ppm): 10.85 (broad, 1H), 8.19 (d, 2H), 7.57 (d, 2H), 6.82 (s, 1H), 2.98 (s, 3H), 2.45 (s, 3H), 2.45-2.37 (m, 4H), 2.03-1.93 (m, 1H), 1.78-1.67 (m, 1H).

LC/MS (method 6, ESIpos): R$_t$=1.06 min, m/z=311 [M+H]$^+$.

Step 5: 5-[1-(3-Bromobenzyl)-5-methyl-1H-pyrazol-3-yl]-3-[4-(1-methoxycyclobutyl)phenyl]-1,2,4-oxadiazole

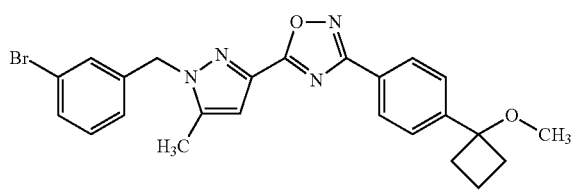 [SMILES: COC1(c2ccc(-c3noc(-c4cc(C)n(Cc5cccc(Br)c5)n4)n3)cc2)CCC1]

Analogously to the process described in Example 1A/Step 2, 250 mg (0.806 mmol) of the compound from Example 7A/Step 4 and 242 mg (0.967 mmol) of 3-bromobenzyl bromide were used to obtain 326 mg (84% of theory) of the title compound. It was possible here to dispense with heating the reaction mixture to 45° C.

$^1$H NMR (400 MHz, CDCl$_3$, δ/ppm): 8.21 (d, 2H), 7.56 (d, 2H), 7.44 (d, 1H), 7.32 (s, 1H), 7.22 (t, 1H), 7.09 (d, 1H), 6.83 (s, 1H), 5.43 (s, 2H), 2.97 (s, 3H), 2.44-2.40 (m, 4H), 2.29 (s, 3H), 2.03-1.93 (m, 1H), 1.78-1.67 (m, 1H).

LC/MS (method 6, ESIpos): R$_t$=1.44 min, m/z=479/481 [M+H]$^+$.

Example 8A

3-{[tert-Butyl(diphenyl)silyl]oxy}azetidine

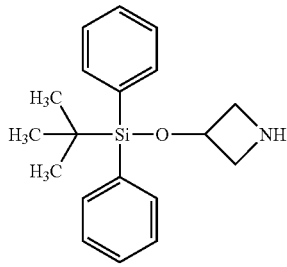 [SMILES: CC(C)(C)[Si](OC1CNC1)(c1ccccc1)c1ccccc1]

Step 1: tert-Butyl 3-{[tert-butyl(diphenyl)silyl]oxy}azetidine-1-carboxylate

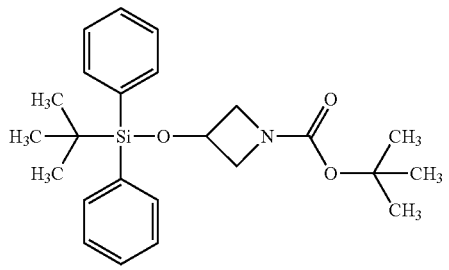 [SMILES: CC(C)(C)OC(=O)N1CC(O[Si](c2ccccc2)(c2ccccc2)C(C)(C)C)C1]

20.0 g (115 mmol) of tert-butyl 3-hydroxyazetidine-1-carboxylate and 9.43 g (139 mmol) of imidazole were initially charged in 200 ml of anhydrous DMF, and 34.91 g (127 mmol) of tert-butyl(diphenyl)silyl chloride were added at RT. After the reaction mixture had been stirred at RT for 18 h, it was poured into 3.2 liters of water and then extracted three times with approx. 1 liter each time of diethyl ether. The combined organic extracts were washed successively with saturated sodium hydrogencarbonate solution, water and saturated sodium chloride solution. After drying over anhydrous magnesium sulphate, the mixture was filtered and the solvent was removed on a rotary evaporator. The remaining residue was stirred with 100 ml of pentane for a few minutes. Subsequently, the solid was filtered off with suction and dried under high vacuum. 29.18 g (61% of theory) of the title compound were obtained.

$^1$H NMR (400 MHz, CDCl$_3$, δ/ppm): 7.60 (d, 4H), 7.46-7.37 (m, 6H), 4.53-4.49 (m, 1H), 3.93 (dd, 2H), 3.87 (dd, 2H), 1.41 (s, 9H), 1.04 (s, 9H).

LC/MS (method 6, ESIpos): R$_t$=1.65 min, m/z=412 [M+H]$^+$.

Step 2: 3-{[tert-Butyl(diphenyl)silyl]oxy}azetidine

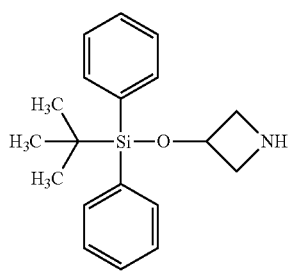 [SMILES: CC(C)(C)[Si](OC1CNC1)(c1ccccc1)c1ccccc1]

70 ml of trifluoroacetic acid (TFA) were added dropwise at RT to a solution of 20.0 g (48.6 mmol) of the compound from Example 8A/Step 1 in 70 ml of dichloromethane. After the reaction mixture had been stirred at RT for 30 min, all volatile components were removed on a rotary evaporator. 1 liter of 1 M sodium hydroxide solution was added to the remaining residue, which was extracted three times with approx. 200 ml each time of dichloromethane. The combined organic extracts were dried over anhydrous magnesium sulphate, filtered and finally concentrated to dryness on a rotary evaporator. After the residue had been dried under high vacuum, 14.85 g (98% of theory) of the title compound were obtained.

$^1$H NMR (400 MHz, CDCl$_3$, δ/ppm): 7.61 (d, 4H), 7.45-7.36 (m, 6H), 4.64-4.58 (m, 1H), 3.68 (dd, 2H), 3.53 (dd, 2H), 2.19 (broad, 1H), 1.03 (s, 9H).

LC/MS (method 6, ESIpos): R$_t$=0.90 min, m/z=312 [M+H]$^+$.

Example 9A

4-{[tert-Butyl(diphenyl)silyl]oxy}piperidine

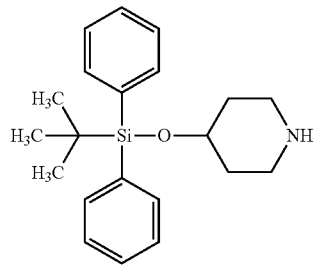

Step 1: tert-Butyl 4-{[tert-butyl(diphenyl)silyl]oxy}piperidine-1-carboxylate

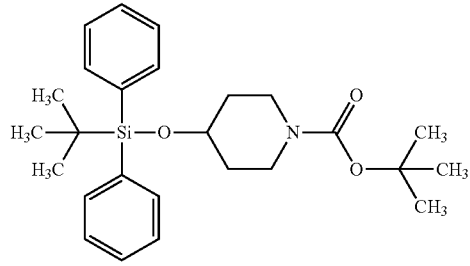 [SMILES: CC(C)(C)OC(=O)N1CCC(O[Si](c2ccccc2)(c2ccccc2)C(C)(C)C)CC1]

10.0 g (49.7 mmol) of tert-butyl 4-hydroxypiperidine-1-carboxylate and 4.06 g (59.7 mmol) of imidazole were initially charged in 100 ml of anhydrous DMF, and 15.02 g (54.7 mmol) of tert-butyl(diphenyl)silyl chloride were added at 0° C. After the reaction mixture had been stirred at RT for 48 h, it was poured into 1.6 liters of water and then extracted three times with approx. 500 ml each time of diethyl ether. The combined organic extracts were washed successively with saturated sodium hydrogencarbonate solution, water and saturated sodium chloride solution. After drying over anhydrous magnesium sulphate, the mixture was filtered and the solvent was removed on a rotary evaporator. The remaining residue was roughly purified by means of suction filtration (approx. 300 g of silica gel, eluent: cyclohexane→2:1 cyclohexane/ethyl acetate). 22.21 g (91% of theory, approx. 90% purity) of the title compound were obtained.

$^1$H NMR (400 MHz, CDCl$_3$, δ/ppm): 7.67 (d, 4H), 7.43-7.37 (m, 6H), 3.93-3.87 (m, 1H), 3.68-3.60 (m, 2H), 3.22-3.14 (m, 2H), 1.63-1.48 (m, 4H), 1.43 (s, 9H), 1.07 (s, 9H).

LC/MS (method 6, ESIpos): R$_t$=1.68 min, m/z=440 [M+H]$^+$.

Step 2: 4-{[tert-Butyl(diphenyl)silyl]oxy}piperidine

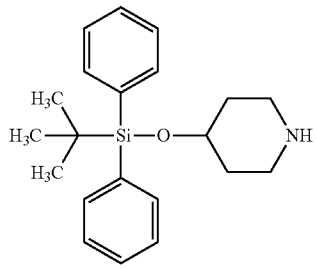 [SMILES: CC(C)(C)[Si](OC1CCNCC1)(c1ccccc1)c1ccccc1]

Analogously to the process described in Example 8A/Step 2, 2.5 g (5.12 mmol, 90% purity) of the compound from Example 9A/Step 1 were used to obtain 1.45 g (83% of theory) of the title compound. In this case, the product was purified by means of MPLC (approx. 50 g of silica gel, eluent: ethyl acetate 9:1 ethyl acetate/triethylamine)

$^1$H NMR (400 MHz, CDCl$_3$, δ/ppm): 7.68 (d, 4H), 7.45-7.35 (m, 6H), 3.83-3.77 (m, 1H), 3.07-3.01 (m, 2H), 2.52-2.47 (m, 2H), 1.72-1.66 (m, 2H), 1.53-1.45 (m, 2H), 1.07 (s, 9H).

LC/MS (method 14, ESIpos): R$_t$=0.87 min, m/z=340 [M+H]$^+$.

Example 10A

5-[1-(3-Bromobenzyl)-5-methyl-1H-pyrazol-3-yl]-3-{4-[(trifluoromethyl)sulphanyl]phenyl}-1,2,4-oxadiazole

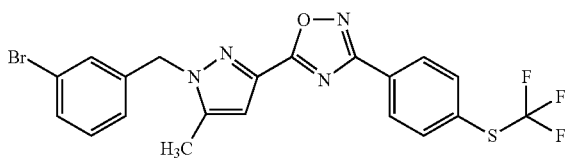

Step 1: N'-Hydroxy-4-[(trifluoromethyl)sulphanyl]benzenecarboximide amide

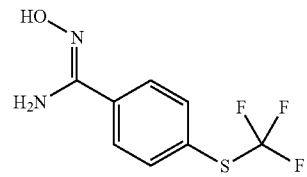 [SMILES: N/C(=N\O)c1ccc(SC(F)(F)F)cc1]

73 g (1.05 mol) of hydroxylammonium chloride were added to a solution of 113 g (500 mmol) of 4-[(trifluoromethyl)sulphanyl]benzenecarbonitrile and 147 ml (1.05 mol) of triethylamine in 1.4 liters of ethanol, and then the mixture was heated under reflux for 30 min. After cooling to RT, 1 liter of water was added and the mixture was extracted three times with a total of 1.4 liters of ethyl acetate. The combined organic extracts were washed successively with water and saturated sodium chloride solution. After drying over anhydrous magnesium sulphate, the mixture was filtered and the solvent was removed on a rotary evaporator. The resulting residue was taken up in 1 liter of cyclohexane, 40 ml of diisopropyl ether were added and the mixture was stirred at RT for 20 min. The resulting solid was filtered off with suction, and, after drying under high vacuum, a first portion of 78.6 g of the title compound was obtained. The filtrate was concentrated and the residue was subsequently stirred at boiling in a mixture of 100 ml of cyclohexane and 5 ml of ethyl acetate for 30 min. After cooling, the solid was filtered off with suction and dried under high vacuum. This gave a second portion of 4.2 g of the title compound. A total of 82.8 g (70% of theory) of the title compound was thus obtained.

$^1$H NMR (400 MHz, DMSO-$d_6$, δ/ppm): 9.90 (s, 1H), 7.80 (d, 2H), 7.72 (d, 2H), 5.94 (s, 2H).

LC/MS (method 2, ESIpos): $R_t$=1.42 min, m/z=237 [M+H]$^+$.

Step 2: 5-(5-Methyl-1H-pyrazol-3-yl)-3-{4-[(trifluoromethyl)sulphanyl]phenyl}-1,2,4-oxadiazole

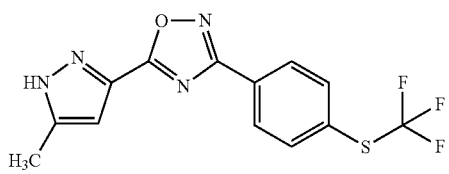 [SMILES: Cc1cc(-c2nc(-c3ccc(SC(F)(F)F)cc3)no2)n[nH]1]

To a suspension of 63.45 g (391 mmol) of 1,1'-carbonyldiimidazole in 235 ml of anhydrous DMF was added dropwise, at RT within 15 min, a solution of 47 g (373 mmol) of 5-methyl-1H-pyrazole-3-carboxylic acid in 235 ml of anhydrous DMF. After the mixture had been stirred at RT for 1 h 45 min, 88 g (373 mmol) of the compound from Example 10A/Step 1 were added. Subsequently, the reaction mixture was heated to 110° C. for 4 h. After cooling to RT, 3.5 liters of water were added gradually while stirring vigorously, as a result of which the product precipitated out. The solid was filtered off with suction and washed with approx. 1 liter of cold water. The crude product was purified by recrystallization from a solvent mixture consisting of 500 ml each of acetonitrile and ethanol. After cooling, filtering and drying under high vacuum, a first portion of 94.2 g of the title compound was obtained. After concentration and another crystallization from 150 ml of ethanol, a further 6.2 g of the title compound were obtained. A total of 100.4 g (83% of theory) of the title compound was thus obtained.

$^1$H NMR (400 MHz, CDCl$_3$, δ/ppm): 10.60 (broad, 1H), 8.23 (d, 2H), 7.79 (d, 2H), 6.81 (s, 1H), 2.47 (s, 3H).

LC/MS (method 6, ESIpos): $R_t$=1.17 min, m/z=327 [M+H]$^+$.

Step 3: 5-[1-(3-Bromobenzyl)-5-methyl-1H-pyrazol-3-yl]-3-{4-[(trifluoromethyl)sulphanyl]phenyl}-1,2,4-oxadiazole

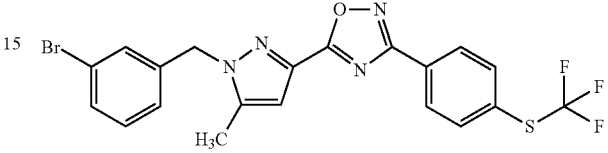

2.24 g (19.9 mmol) of solid potassium tert-butoxide were added at RT to a solution of 5.0 g (15.3 mmol) of the compound from Example 10A/Step 2 and 4.60 g (18.4 mmol) of 3-bromobenzyl bromide in 150 ml of anhydrous dioxane. The reaction mixture was stirred at RT for 16 h. Subsequently, approx. 50-100 ml of the solvent was removed on a rotary evaporator. The remaining residue was diluted with 900 ml of ethyl acetate and washed three times with 200 ml each time of water and finally once with 200 ml of saturated sodium chloride solution. After drying over anhydrous magnesium sulphate and filtration, the solvent was removed on a rotary evaporator. The resulting crude product was recrystallized from cyclohexane. After the solid had been filtered off with suction and dried, 5.03 g (66% of theory) of the title compound were obtained.

$^1$H NMR (400 MHz, CDCl$_3$, δ/ppm): 8.27 (d, 2H), 7.78 (d, 2H), 7.44 (d, 1H), 7.32 (s, 1H), 7.22 (t, 1H), 7.09 (d, 1H), 6.84 (s, 1H), 5.43 (s, 2H), 2.29 (s, 3H).

LC/MS (method 6, ESIpos): $R_t$=1.49 min, m/z=495/497 [M+H]$^+$.

Example 11A (S)-1-{3-[(5-Methyl-3-{3-[4-(trifluoromethoxy)phenyl]-1,2,4-oxadiazol-5-yl}-1H-pyrazol-1-yl)methyl]phenyl}azetidin-3-yl N-(tert-butoxycarbonyl)-L-valinate

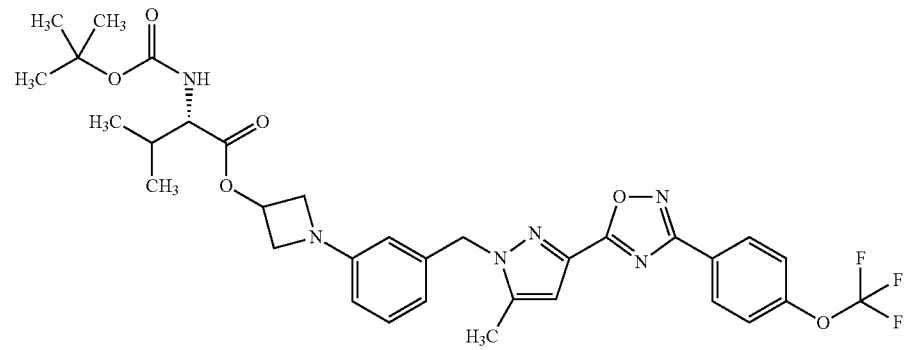 [SMILES: Cc1cc(-c2nc(-c3ccc(OC(F)(F)F)cc3)no2)nn1Cc1cccc(N2CC(OC(=O)[C@@H](NC(=O)OC(C)(C)C)C(C)C)C2)c1]

117 mg (0.955 mmol) of 4-N,N-dimethylaminopyridine and 915 mg (4.77 mmol) of EDC were added to a solution of 750 mg (1.59 mmol) of the compound from Example 1 (see section for the Working Examples) and 691 mg (3.18 mmol) of (S)—N-(tert-butoxycarbonyl)-L-valine in 30 ml of dichloromethane. After the reaction mixture had been stirred at RT for 2 h, it was diluted with 100 ml of dichloromethane and washed twice with 100 ml each time of water and once with 100 ml of saturated sodium chloride solution. After drying over anhydrous magnesium sulphate, filtration and concentration, the product was isolated by means of MPLC (approx. 100 g of silica gel, eluent: 4:1→3:1 cyclohexane/ethyl acetate). 671 mg (90% of theory) of the title compound were obtained.

$^1$H NMR (400 MHz, CDCl$_3$, δ/ppm): 8.27 (d, 2H), 7.33 (d, 2H), 7.19 (t, 1H), 6.81 (s, 1H), 6.56 (d, 1H), 6.38 (d, 1H), 6.24 (s, 1H), 5.39 (s, 2H), 5.37-5.31 (m, 1H), 4.95 (d, broad, 1H), 4.24-4.18 (m, 3H), 3.83-3.73 (m, 2H), 2.28 (s, 3H), 2.20-2.11 (m, 1H), 1.43 (s, 9H), 0.98 (d, 3H), 0.90 (d, 3H).

LC/MS (method 14, ESIpos): R$_t$=1.53 min, m/z=671 [M+H]$^+$.

WORKING EXAMPLES

Example 1

1-{3-[(5-Methyl-3-{3-[4-(trifluoromethoxy)phenyl]-1,2,4-oxadiazol-5-yl}-1H-pyrazol-1-yl)methyl]phenyl}azetidin-3-ol

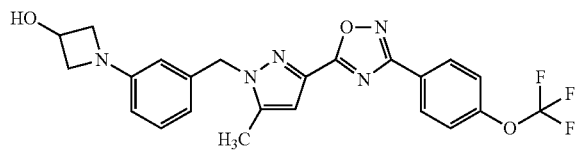 [SMILES: Cc1cc(-c2nc(-c3ccc(OC(F)(F)F)cc3)no2)nn1Cc1cccc(N2CC(O)C2)c1]

A mixture of 2.0 g (4.17 mmol) of the compound from Example 1A, 1.95 g (6.26 mmol) of the compound from Example 8A, 256 mg (0.280 mmol) of tris(dibenzylideneacetone)dipalladium(0), 398 mg (0.835 mmol) of 2-dicyclohexylphosphino-2',4',6'-triisopropylbiphenyl (X-Phos) and 2.72 g (8.35 mmol) of caesium carbonate in 20 ml of anhydrous DMF was heated to 120° C. under argon in a microwave oven (Biotage Initiator, dynamic control of the incident power) for 2.5 h. After cooling to RT, 100 ml of water were added to the reaction mixture, which was extracted three times with approx. 100 ml each time of ethyl acetate. The combined organic extracts were washed successively with water and saturated sodium chloride solution, dried over anhydrous magnesium sulphate, filtered and finally freed of the solvent on a rotary evaporator. The remaining residue was dissolved in 40 ml of THF, and 6.3 ml (6.26 mmol) of a 1 M solution of tetra-n-butylammonium fluoride (TBAF) in THF were added. After this mixture had been stirred at RT for 1 h, it was subjected to aqueous workup in the same way as described above. The remaining residue was purified by suction filtration through 200 g of silica gel with 2:1 (3 liters)→1:1 (3 liters) cyclohexane/ethyl acetate as the eluent. After concentration and drying under a high vacuum, 1.56 g (79% of theory) of the title compound were obtained.

$^1$H NMR (400 MHz, CDCl$_3$, δ/ppm): 8.25 (d, 2H), 7.33 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.13 (dd, 2H), 3.63 (dd, 2H), 2.27 (s, 3H), 2.12 (d, 1H).

LC/MS (method 6, ESIpos): R$_t$=1.20 min, m/z=472 [M+H]$^+$.

Example 2

1-(3-{[5-Methyl-3-(3-{4-[1-(trifluoromethyl)cyclopropyl]phenyl}-1,2,4-oxadiazol-5-yl)-1H-pyrazol-1-yl]methyl}phenyl)azetidin-3-ol

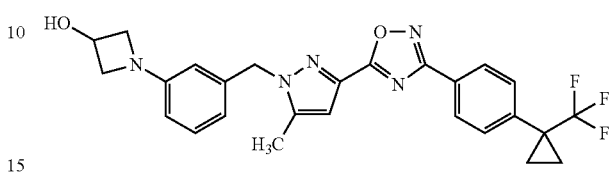

Analogously to the process described in Example 1, 500 mg (0.993 mmol) of the compound from Example 2A and 464 mg (1.49 mmol) of the compound from Example 8A were used to obtain 289 mg (58% of theory) of the title compound. It was possible here to dispense with the second component step of the process (silyl ether cleavage with TBAF), since the protecting group had already been detached in the course of the first component step. The crude product was purified by means of MPLC (silica gel, eluent: 1:1 cyclohexane/ethyl acetate) and subsequent extractive stirring in a mixture of 25 ml of pentane, 1 ml of diisopropyl ether and 125 μl of dichloromethane.

$^1$H NMR (400 MHz, CDCl$_3$, δ/ppm): 8.19 (d, 2H), 7.58 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.13 (dd, 2H), 3.63 (dd, 2H), 2.27 (s, 3H), 2.01 (d, 1H), 1.42-1.39 (m, 2H), 1.10-1.07 (m, 2H).

LC/MS (method 6, ESIpos): R$_t$=1.26 min, m/z=496 [M+H]$^+$.

Example 3

1-{3-[(5-Methyl-3-{3-[4-(1,1,1-trifluoro-2-methylpropan-2-yl)phenyl]-1,2,4-oxadiazol-5-yl}-1H-pyrazol-1-yl)methyl]phenyl}azetidin-3-ol

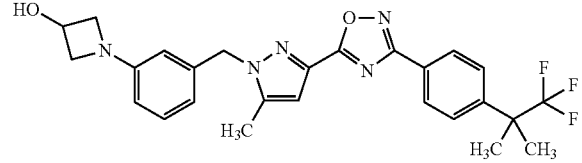 [SMILES: Cc1cc(-c2nc(-c3ccc(C(C)(C)C(F)(F)F)cc3)no2)nn1Cc1cccc(N2CC(O)C2)c1]

Analogously to the process described in Example 1, 150 mg (0.297 mmol) of the compound from Example 3A and 139 mg (0.445 mmol) of the compound from Example 8A were used to obtain 68 mg (46% of theory) of the title compound. The reaction time in the first component step of the process here was 1 h. The crude product was purified by means of preparative HPLC (method 13). The free base was obtained from the resulting formate salt of the title compound by percolation of a methanolic solution of the salt through a hydrogencarbonate cartridge (from Polymerlabs, Stratospheres SPE, PL-HCO$_3$ MP SPE, capacity 0.9 mmol). The final purification was effected by extractive stirring in a mixture of 3 ml of pentane and a few drops of diisopropyl ether.

¹H NMR (400 MHz, CDCl₃, δ/ppm): 8.20 (d, 2H), 7.63 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.13 (dd, 2H), 3.63 (dd, 2H), 2.27 (s, 3H), 2.18 (d, 1H), 1.62 (s, 6H).

LC/MS (method 6, ESIpos): R$_f$=1.27 min, m/z=498 [M+H]⁺.

Example 4

1-{3-[(5-Methyl-3-{3-[4-(tetrahydro-2H-pyran-4-yl)phenyl]-1,2,4-oxadiazol-5-yl}-1H-pyrazol-1-yl)methyl]phenyl}azetidin-3-ol

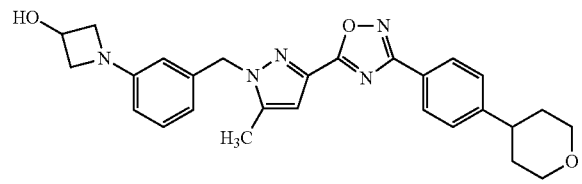 [SMILES: Cc1cc(-c2nc(-c3ccc(C4CCOCC4)cc3)no2)nn1Cc1cccc(N2CC(O)C2)c1]

Analogously to the process described in Example 3, 150 mg (0.313 mmol) of the compound from Example 4A and 146 mg (0.469 mmol) of the compound from Example 8A were used to obtain 77 mg (52% of theory) of the title compound.

¹H NMR (400 MHz, CDCl₃, δ/ppm): 8.17 (d, 2H), 7.36 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.15-4.07 (m, 4H), 3.63 (dd, 2H), 3.55 (dt, 2H), 2.87-2.78 (m, 1H), 2.26 (s, broad, 4H), 1.91-1.78 (m, 4H).

LC/MS (method 4, ESIpos): R$_t$=1.27 min, m/z=472 [M+H]⁺.

Example 5

1-{3-[(3-{3-[4-(4-Fluorotetrahydro-2H-pyran-4-yl)phenyl]-1,2,4-oxadiazol-5-yl}-5-methyl-1H-pyrazol-1-yl)methyl]phenyl}azetidin-3-ol

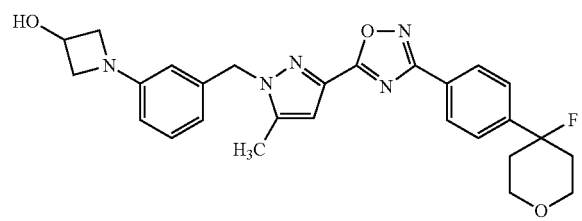 [SMILES: Cc1cc(-c2nc(-c3ccc(C4(F)CCOCC4)cc3)no2)nn1Cc1cccc(N2CC(O)C2)c1]

Analogously to the process described in Example 3, 150 mg (0.302 mmol) of the compound from Example 5A and 141 mg (0.452 mmol) of the compound from Example 8A were used to obtain 62 mg (42% of theory) of the title compound.

¹H NMR (400 MHz, CDCl₃, δ/ppm): 8.23 (d, 2H), 7.53 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.13 (dd, 2H), 4.00-3.87 (m, 4H), 3.63 (dd, 2H), 2.27 (d, 1H), 2.26 (s, 3H), 2.29-2.12 (m, 2H), 1.99-1.90 (m, 2H).

LC/MS (method 4, ESIpos): R$_t$=1.28 min, m/z=490 [M+H]⁺.

Example 6

1-{3-[(3-{3-[4-(3-Fluorooxetan-3-yl)phenyl]-1,2,4-oxadiazol-5-yl}-5-methyl-1H-pyrazol-1-yl)methyl]phenyl}azetidin-3-ol

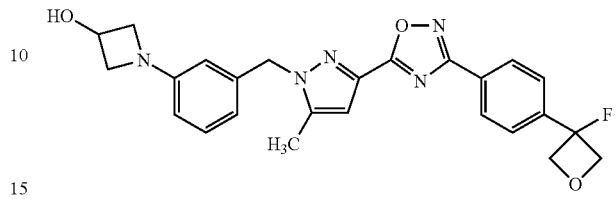

Analogously to the process described in Example 3, 150 mg (0.320 mmol) of the compound from Example 6A and 149 mg (0.479 mmol) of the compound from Example 8A were used to obtain 60 mg (39% of theory) of the title compound.

¹H NMR (400 MHz, CDCl₃, δ/ppm): 8.29 (d, 2H), 7.71 (d, 2H), 7.17 (t, 1H), 6.81 (s, 1H), 6.53 (d, 1H), 6.39 (d, 1H), 6.27 (s, 1H), 5.39 (s, 2H), 5.06 (dd, 2H), 5.00 (dd, 2H), 4.77-4.70 (m, 1H), 4.13 (dd, 2H), 3.63 (dd, 2H), 2.29 (d, 1H), 2.27 (s, 3H).

LC/MS (method 4, ESIpos): R$_t$=1.22 min, m/z=462 [M+H]⁺.

Example 7

1-{3-[(3-{3-[4-(1-Methoxycyclobutyl)phenyl]-1,2,4-oxadiazol-5-yl}-5-methyl-1H-pyrazol-1-yl)methyl]phenyl}azetidin-3-ol

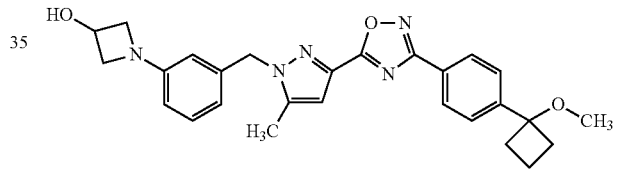

Analogously to the process described in Example 3, 150 mg (0.313 mmol) of the compound from Example 7A and 146 mg (0.469 mmol) of the compound from Example 8A were used to obtain 53 mg (36% of theory) of the title compound.

¹H NMR (400 MHz, CDCl₃, δ/ppm): 8.22 (d, 2H), 7.56 (d, 2H), 7.17 (t, 1H), 6.80 (s, 1H), 6.53 (d, 1H), 6.39 (d, 1H), 6.27 (s, 1H), 5.38 (s, 2H), 4.77-4.70 (m, 1H), 4.13 (dd, 2H), 3.63 (dd, 2H), 2.97 (s, 3H), 2.46-2.39 (m, 4H), 2.27 (s, 3H), 2.21 (d, 1H), 2.03-1.93 (m, 1H), 1.78-1.67 (m, 1H).

LC/MS (method 6, ESIpos): R$_t$=1.21 min, m/z=472 [M+H]⁺.

Example 8

1-{3-[(5-Methyl-3-{3-[4-(trifluoromethoxy)phenyl]-1,2,4-oxadiazol-5-yl}-1H-pyrazol-1-yl)methyl]phenyl}piperidin-4-ol

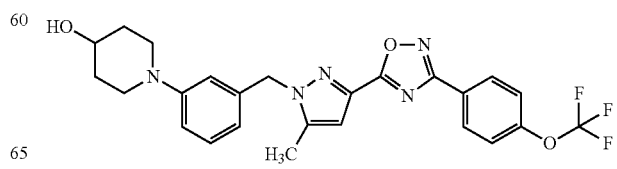

A mixture of 150 mg (0.313 mmol) of the compound from Example 1A, 63 mg (0.626 mmol) of 4-hydroxypiperidine, 19 mg (0.021 mmol) of tris(dibenzylideneacetone)dipalladium(0), 30 mg (0.063 mmol) of 2-dicyclohexylphosphino-2′,4′,6′-triisopropylbiphenyl (X-Phos) and 254 mg (0.782 mmol) of caesium carbonate in 3 ml of anhydrous DMF was stirred at 80° C. under argon for 12 h. After cooling to RT, the reaction mixture was filtered through a little Celite and the filtrate was then separated into its components by means of preparative HPLC (method 11). After concentration of the product fractions and drying under high vacuum, 36 mg (23% of theory) of the title compound were obtained.

$^1$H NMR (400 MHz, CDCl$_3$, δ/ppm): 8.27 (d, 2H), 7.34 (d, 2H), 7.21 (t, 1H), 6.86 (d, 1H), 6.81 (s, 1H), 6.75 (s, 1H), 6.61 (d, 1H), 5.40 (s, 2H), 3.87-3.81 (m, 1H), 3.53-3.49 (m, 2H), 2.90 (dt, 2H), 2.28 (s, 3H), 2.01-1.95 (m, 2H), 1.70-1.61 (m, 3H).

LC/MS (method 6, ESIpos): R$_t$=1.18 min, m/z=500 [M+H]$^+$.

Example 9

1-(3-{[5-Methyl-3-(3-{4-[1-(trifluoromethyl)cyclopropyl]phenyl}-1,2,4-oxadiazol-5-yl)-1H-pyrazol-1-yl]methyl}phenyl)piperidin-4-ol

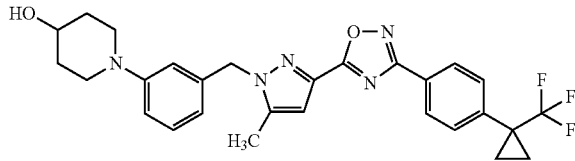

Analogously to the process described in Example 3, 125 mg (0.248 mmol) of the compound from Example 2A and 50 mg (0.497 mmol) of 4-hydroxypiperidine were used to obtain 20 mg (16% of theory) of the title compound. The first component step of the process was effected here at a reaction temperature of 130° C. The preparative HPLC purification was performed by method 11

$^1$H NMR (400 MHz, CDCl$_3$, δ/ppm): 8.18 (d, 2H), 7.59 (d, 2H), 7.20 (t, 1H), 6.86 (d, 1H), 6.80 (s, 1H), 6.75 (s, 1H), 6.61 (d, 1H), 5.40 (s, 2H), 3.87-3.81 (m, 1H), 3.53-3.49 (m, 2H), 2.90 (dt, 2H), 2.27 (s, 3H), 2.01-1.94 (m, 2H), 1.70-1.60 (m, 3H), 1.43-1.39 (m, 2H), 1.10-1.07 (m, 2H).

LC/MS (method 4, ESIpos): R$_t$=1.39 min, m/z=524 [M+H]$^+$.

Example 10

1-{3-[(5-Methyl-3-{3-[4-(1,1,1-trifluoro-2-methylpropan-2-yl)phenyl]-1,2,4-oxadiazol-5-yl}-1H-pyrazol-1-yl)methyl]phenyl}piperidin-4-ol

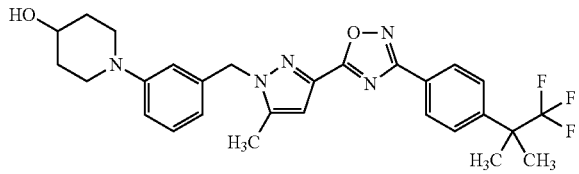 [SMILES: Cc1cc(-c2nc(-c3ccc(C(C)(C)C(F)(F)F)cc3)no2)nn1Cc1cccc(N2CCC(O)CC2)c1]

Analogously to the process described in Example 9, 125 mg (0.247 mmol) of the compound from Example 3A and 50 mg (0.495 mmol) of 4-hydroxypiperidine were used to obtain 16 mg (12% of theory) of the title compound.

$^1$H NMR (400 MHz, CDCl$_3$, δ/ppm): 8.20 (d, 2H), 7.62 (d, 2H), 7.20 (t, 1H), 6.86 (d, 1H), 6.80 (s, 1H), 6.75 (s, 1H), 6.61 (d, 1H), 5.40 (s, 2H), 3.88-3.80 (m, 1H), 3.54-3.48 (m, 2H), 2.90 (dt, 2H), 2.27 (s, 3H), 2.01-1.94 (m, 2H), 1.69-1.64 (m, 2H), 1.62 (s, 6H), 1.43 (d, 1H).

LC/MS (method 6, ESIpos): R$_t$=1.20 min, m/z=526 [M+H]$^+$.

Example 11

1-{3-[(5-Methyl-3-{3-[4-(trifluoromethoxy)phenyl]-1,2,4-oxadiazol-5-yl}-1H-pyrazol-1-yl)methyl]phenyl}piperidine-4-carbonitrile

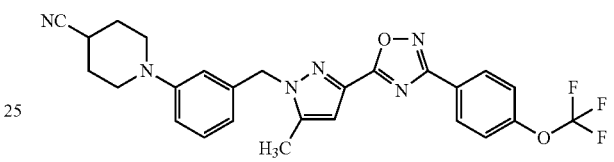

Analogously to the process described in Example 8, 150 mg (0.313 mmol) of the compound from Example 1A and 69 mg (0.626 mmol) of 4-cyanopiperidine were used to obtain 68 mg (43% of theory) of the title compound.

$^1$H NMR (400 MHz, CDCl$_3$, δ/ppm): 8.26 (d, 2H), 7.34 (d, 2H), 7.23 (t, 1H), 6.86 (d, 1H), 6.81 (s, 1H), 6.74 (s, 1H), 6.67 (d, 1H), 5.40 (s, 2H), 3.41-3.34 (m, 2H), 3.11-3.03 (m, 2H), 2.81-2.75 (m, 1H), 2.28 (s, 3H), 2.07-1.92 (m, 4H).

LC/MS (method 2, ESIpos): R$_t$=2.79 min, m/z=509 [M+H]$^+$.

Example 12

1-(3-{[5-Methyl-3-(3-{4-[1-(trifluoromethyl)cyclopropyl]phenyl}-1,2,4-oxadiazol-5-yl)-1H-pyrazol-1-yl]methyl}phenyl)piperidine-4-carbonitrile

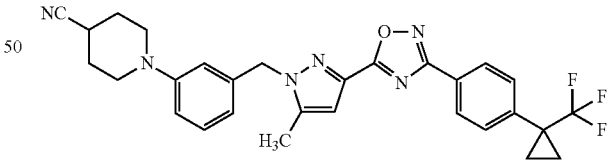

Analogously to the process described in Example 9, 50 mg (0.099 mmol) of the compound from Example 2A and 22 mg (0.199 mmol) of 4-cyanopiperidine were used to obtain 23 mg (43% of theory) of the title compound.

$^1$H NMR (400 MHz, CDCl$_3$, δ/ppm): 8.19 (d, 2H), 7.58 (d, 2H), 7.22 (t, 1H), 6.84 (d, 1H), 6.81 (s, 1H), 6.73 (s, 1H), 6.67 (d, 1H), 5.40 (s, 2H), 3.41-3.34 (m, 2H), 3.10-3.03 (m, 2H), 2.80-2.74 (m, 1H), 2.28 (s, 3H), 2.07-1.92 (m, 4H), 1.42-1.39 (m, 2H), 1.11-1.07 (m, 2H).

LC/MS (method 6, ESIpos): R$_t$=1.37 min, m/z=533 [M+H]$^+$.

Example 13

1-{3-[(5-Methyl-3-{3-[4-(1,1,1-trifluoro-2-methyl-propan-2-yl)phenyl]-1,2,4-oxadiazol-5-yl}-1H-pyrazol-1-yl)methyl]phenyl}piperidine-4-carbonitrile

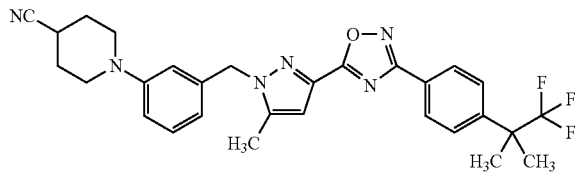 [SMILES: Cc1cc(-c2nc(-c3ccc(C(C)(C)C(F)(F)F)cc3)no2)nn1Cc1cccc(N2CCC(C#N)CC2)c1]

Analogously to the process described in Example 9, 125 mg (0.247 mmol) of the compound from Example 3A and 55 mg (0.495 mmol) of 4-cyanopiperidine were used to obtain 66 mg (50% of theory) of the title compound.

$^1$H NMR (400 MHz, CDCl$_3$, δ/ppm): 8.20 (d, 2H), 7.62 (d, 2H), 7.22 (t, 1H), 6.84 (d, 1H), 6.81 (s, 1H), 6.73 (s, 1H), 6.67 (d, 1H), 5.40 (s, 2H), 3.40-3.34 (m, 2H), 3.10-3.03 (m, 2H), 2.80-2.74 (m, 1H), 2.28 (s, 3H), 2.07-1.91 (m, 4H), 1.63 (s, 6H).

LC/MS (method 6, ESIpos): R$_t$=1.38 min, m/z=535 [M+H]$^+$.

Example 14

1-(3-{[5-Methyl-3-(3-{4-[(trifluoromethyl)sulpha-nyl]phenyl}-1,2,4-oxadiazol-5-yl)-1H-pyrazol-1-yl]methyl}phenyl)piperidin-4-ol

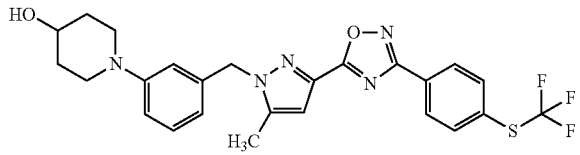 [SMILES: Cc1cc(-c2nc(-c3ccc(SC(F)(F)F)cc3)no2)nn1Cc1cccc(N2CCC(O)CC2)c1]

A mixture of 500 mg (1.01 mmol) of the compound from Example 10A, 514 mg (1.51 mmol) of the compound from Example 9A, 92 mg (0.101 mmol) of tris(dibenzylideneacetone)dipalladium(0), 96 mg (0.202 mmol) of 2-dicyclohexylphosphino-2',4',6'-triisopropylbiphenyl (X-Phos) and 194 mg (2.02 mmol) of sodium tert-butoxide in 10 ml of toluene was heated to 80° C. under argon in a microwave oven (Biotage Initiator, dynamic control of the incident power) for 3 h. After cooling to RT, 100 ml of water were added to the reaction mixture, which was extracted three times with approx. 100 ml each time of ethyl acetate. The combined organic extracts were washed successively with water and saturated sodium chloride solution, dried over anhydrous magnesium sulphate, filtered and finally freed of the solvent on a rotary evaporator. The resulting crude product, which was the corresponding silyl-protected intermediate, was purified by means of MPLC (approx. 70 g of silica gel, eluent: cyclohexane→5:1 cyclohexane/ethyl acetate). Subsequently, this product was dissolved in 3.5 ml of THF, and 3.5 ml (3.5 mmol) of a 1 M solution of tetra-n-butylammonium fluoride (TBAF) in THF were added. After this mixture had been stirred at RT for 20 min, it was concentrated on a rotary evaporator. The title compound was isolated by means of MPLC (approx. 20 g of silica gel, eluent: 2:1→1:3 cyclohexane/ethyl acetate). After concentration and drying, the product was once again stirred with pentane/diethyl ether. 65 mg (12% of theory) of the title compound were thus obtained.

$^1$H NMR (400 MHz, CDCl$_3$, δ/ppm): 8.27 (d, 2H), 7.78 (d, 2H), 7.21 (t, 1H), 6.87 (d, 1H), 6.81 (s, 1H), 6.75 (s, 1H), 6.61 (d, 1H), 5.40 (s, 2H), 3.88-3.81 (m, 1H), 3.54-3.49 (m, 2H), 2.90 (dt, 2H), 2.29 (s, 3H), 2.01-1.94 (m, 2H), 1.69-1.61 (m, 3H).

LC/MS (method 6, ESIpos): R$_t$=1.25 min, m/z=516 [M+H]$^+$.

Example 15

1-{3-[(5-Methyl-3-{3-[4-(trifluoromethoxy)phenyl]-1,2,4-oxadiazol-5-yl}-1H-pyrazol-1-yl)methyl]phenyl}azetidin-3-yl N,N-dimethylglycinate

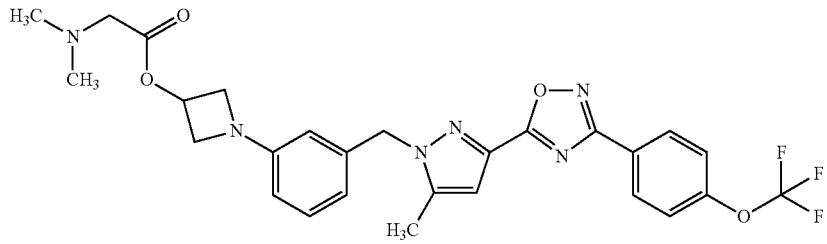 [SMILES: Cc1cc(-c2nc(-c3ccc(OC(F)(F)F)cc3)no2)nn1Cc1cccc(N2CC(OC(=O)CN(C)C)C2)c1]

86 mg (0.70 mmol) of 4-N,N-dimethylaminopyridine and 671 mg (3.50 mmol) of EDC were added to a solution of 550 mg (1.17 mmol) of the compound from Example 1 and 361 mg (3.50 mmol) of N,N-dimethylglycine in 11 ml of dichloromethane. After the reaction mixture had been stirred at RT for 8 h, all volatile constituents were removed on a rotary evaporator. The residue obtained was taken up in 200 ml of ethyl acetate and washed once with approx. 100 ml of water. After drying over anhydrous magnesium sulphate, filtration and concentration, the product was isolated by means of MPLC (approx. 30 g of silica gel, eluent: 25:25:1 cyclohexane/ethyl acetate/triethylamine) A first fraction of 328 mg of the title compound was obtained. A further 115 mg of the title compound were obtained from a second, still-contaminated fraction by recrystallization from cyclopentyl methyl ether. A total of 443 mg (68% of theory) of the title compound was thus obtained. Another crystallization from diisopropyl ether/cyclopentyl methyl ether (2:1, 1.5 ml per 100 mg) gave the title compound with a melting point of 117° C.

$^1$H NMR (400 MHz, CDCl$_3$, δ/ppm): 8.26 (d, 2H), 7.33 (d, 2H), 7.18 (t, 1H), 6.81 (s, 1H), 6.55 (d, 1H), 6.39 (d, 1H), 6.24 (s, 1H), 5.39 (s, 2H), 5.38-5.32 (m, 1H), 4.21 (dd, 2H), 3.79 (dd, 2H), 3.20 (s, 2H), 2.36 (s, 6H), 2.28 (s, 3H).

LC/MS (method 6, ESIpos): R$_t$=0.95 min, m/z=557 [M+H]$^+$.

Example 16

(S)-1-{3-[(5-Methyl-3-{3-[4-(trifluoromethoxy)phenyl]-1,2,4-oxadiazol-5-yl}-1H-pyrazol-1-yl)methyl]phenyl}azetidin-3-yl L-valinate

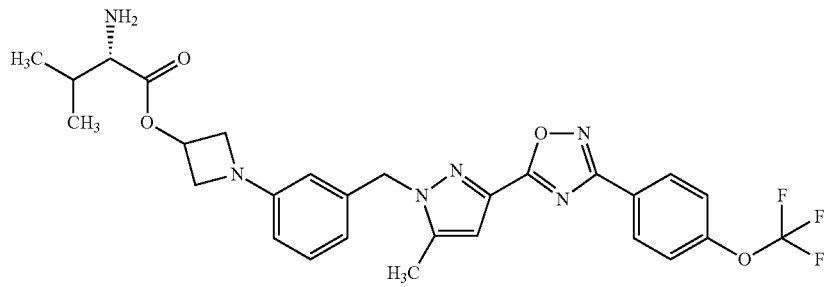 [SMILES: Cc1cc(-c2nc(-c3ccc(OC(F)(F)F)cc3)no2)nn1Cc1cccc(N2CC(OC(=O)[C@@H](N)C(C)C)C2)c1]

25 ml of trifluoroacetic acid (TFA) were added at 0° C. to a solution of 965 mg (1.44 mmol) of the compound from Example 11A in 45 ml of dichloromethane. The reaction mixture was stirred at RT for 1 h. Thereafter, all volatile constituents were removed on a rotary evaporator and the residue obtained was dissolved again in 500 ml of dichloromethane. The product was washed twice with approx. 100 ml each time of saturated sodium hydrogencarbonate solution, then once with 100 ml of water and finally once with 100 ml of saturated sodium chloride solution. After drying over anhydrous magnesium sulphate, the mixture was filtered and the solvent was removed on a rotary evaporator. The resulting crude product (780 mg) was stirred in a mixture of 40 ml of pentane, 2 ml of diisopropyl ether and a few drops of dichloromethane. After the solid had been filtered off with suction and dried under high vacuum, 659 mg (80% of theory) of the title compound were thus obtained.

$^1$H NMR (400 MHz, CDCl$_3$, δ/ppm): 8.27 (d, 2H), 7.33 (d, 2H), 7.19 (t, 1H), 6.80 (s, 1H), 6.57 (d, 1H), 6.39 (d, 1H), 6.25 (s, 1H), 5.39 (s, 2H), 5.35-5.30 (m, 1H), 4.24-4.20 (m, 2H), 3.80-3.74 (m, 2H), 3.32 (d, 1H), 2.28 (s, 3H), 2.12-2.00 (m, 1H), 0.98 (d, 3H), 0.91 (d, 3H).

LC/MS (method 14, ESIpos): R$_t$=0.96 min, m/z=571 [M+H]$^+$.

B. Assessment of Pharmacological Activity

The pharmacological activity of the inventive compounds can be demonstrated by in vitro and in vivo studies, as known to the person skilled in the art. The usefulness of the inventive substances can be illustrated by way of example by in vitro (tumour) cell experiments and in vivo tumour models, as described below. The connection between inhibition of the HIF transcription activity and the inhibition of tumour growth has been demonstrated by numerous studies described in the literature (cf., for example Warburg, 1956; Semenza, 2007).

B-1. HIF Luciferase Assay

HCT 116 cells were stably transfected with a plasmid which contained a luciferase reporter under the control of an HIF-responsive sequence. These cells were sown in microtitre plates [20 000 cells/cavity in RPMI 1640 medium with 10% foetal calf serum (FCS) and 100 μg/ml of hygromycin]. They were incubated overnight under standard conditions (5% CO$_2$, 21% O$_2$, 37° C., moistened). The following morning the cells were incubated with different concentrations of the test substances (0-10 μmol/l) in a hypoxia chamber (1% O$_2$). After 24 h, Bright Glo reagent (Promega, Wis., USA) was added in accordance with the manufacturer's instructions, and after 5 min the luminescence was measured. Cells which were incubated under normoxia served as background controls.

The IC$_{50}$ values from this assay are listed in the following table for representative working examples:

| Example No. | IC$_{50}$ [nmol/L] |
|---|---|
| 1 | 0.7 |
| 2 | 0.6 |
| 3 | 0.6 |
| 8 | 0.6 |
| 9 | 0.5 |
| 10 | 0.4 |
| 11 | 0.4 |
| 12 | 0.3 |
| 13 | 0.3 |
| 14 | 0.5 |

The compound 5-[5-methyl-1-(4-methylbenzyl)-1H-pyrazol-3-yl]-3-[4-(trifluoromethoxy)phenyl]-1,2,4-oxadiazole, described as Example 1 in WO 2008/141731-A2, which, unlike the inventive compounds, does not have a heterocyclyl substituent on the benzyl head group, exhibits an IC$_{50}$ value in this assay of 30 nmol/l.

B-2. Suppression of HIF Target Genes in Vitro:

Human bronchial carcinoma cells (H460 and A549) were incubated for 16 h with variable concentrations of the test substances (1 nM to 10 μM) under normoxic conditions and under partial oxygen pressure 1% (see HIF luciferase assay). The total RNA was isolated from the cells and transcribed into cDNA, and the mRNA expression of HIF target genes was analysed in real-time PCR. Active test substances already lower the mRNA expression of the HIF target genes compared with untreated cells under normoxic conditions, but in particular under hypoxic conditions.

B-3. Human Xenograft Tumour Model:

Human tumour xenograft models in immunodeficient mice were used to assess the substances. For this purpose, tumour cells were cultured in vitro and implanted subcutaneously, or tumour xenotransplant pieces were transplanted further subcutaneously. The animals were treated by oral, subcutaneous or intraperitoneal therapy after the tumour had been established. The activity of the test substances was analysed in monotherapy and in combination therapy with other pharmacological active substances. In addition, the tumour inhibitory potency of test substances on tumours of advanced size (approx. 100 mm²) was characterized. The state of health of the animals was checked daily, and the treatments were performed in accordance with animal welfare regulations. The tumour area was measured with slide gauges (length L, breadth B=shorter dimension). The tumour volume was calculated by the formula (L×B²)/2. The inhibition in tumour growth was determined at the end of the study as the T/C ratio of the tumour areas or tumour weights and as the TGI value (tumour growth inhibition, calculated by the formula [1−(T/C)]×100) (T=tumour size in the treated group; C=tumour size in the untreated control group).

The influence of test substances on the tumour vessel architecture and the blood flow within the tumour was identified with the aid of computer microtomography and ultrasound microstudies on treated and untreated tumour-carrying mice.

C. Determination of Pharmacokinetic Parameters

The pharmacokinetic parameters of the inventive compounds after intravenous or peroral administration can be determined as follows:

The substance to be examined was administered to animals (for example mice or rats) intravenously as a solution (for example in corresponding plasma with a small addition of DMSO or in a PEG/ethanol/water mixture), and peroral administration was effected as a solution (for example in Solutol/ethanol/water or PEG/ethanol/water mixtures) or as a suspension (e.g. in tylose), in each case via a gavage. After administration of the substance, blood was taken from the animals at fixed times. The blood was heparinized, then plasma was obtained therefrom by centrifugation. The substance was quantified analytically in the plasma via LC-MS/MS. From the plasma concentration/time plots determined in this way, using an internal standard and with the aid of a validated computer program, the pharmacokinetic parameters, such as AUC (area under the concentration/time curve), $C_{max}$ (maximum plasma concentration), $t_{1/2}$ (half life), $V_{SS}$ (distribution volume) and CL (clearance), and the absolute and relative bioavailability F and $F_{rel}$ (i.v./p.o. comparison or comparison of suspension to solution after p.o. administration), were calculated.

To determine the active ingredient release from a prodrug compound, the prodrug was administered either intravenously or perorally, as described above, and the concentrations both of the prodrug and of the active ingredient released were quantified in the processed plasma.

C-1. Pharmacokinetic Parameters After Intravenous Administration in Rats:

The substance to be examined was administered intravenously to rats, in each case in amounts between 0.3 and 1.0 mg/kg as a solution in plasma which contained up to 2% DMSO. The kinetic parameters determined for Working Examples 1 and 14 are shown below by way of example for the inventive compounds [$CL_{plasma}$=plasma clearance]:

| Example No. | $t_{1/2}$ [h] | $CL_{plasma}$ [l/h/kg] | $V_{SS}$ [l/kg] |
|---|---|---|---|
| 1 | 6.8 | 1.6 | 12 |
| 14 | 8.2 | 0.72 | 7.8 |

The compound 5-[5-methyl-1-(4-methylbenzyl)-1H-pyrazol-3-yl]-3-[4-(trifluoromethoxy)phenyl]-1,2,4-oxadiazole, described as Example 1 in WO 2008/141731-A2, which, unlike the inventive compounds, does not have a heterocyclyl substituent on the benzyl head group, exhibits the following data for this parameter after intravenous administration in rats: $t_{1/2}$=30 h, $CL_{plasma}$=0.4 l/h/kg, $V_{SS}$=6.9 l/kg.

C-2. Pharmacokinetic Parameters After Peroral Administration in Rats:

The substance to be examined was administered perorally to rats, in each case in amounts between 1 and 3 mg/kg as a solution in Solutol/ethanol/water (40:10:50 or 40:20:40). The kinetic parameters determined for Working Example 1 are shown below by way of example for the inventive compounds [$AUC_{norm}$=dose-normalized exposure (area under the concentration/time curve)]:

| Example No. | $t_{1/2}$ [h] | $AUC_{norm}$ [kg · h/l] | F [%] |
|---|---|---|---|
| 1 | 12 | 0.43 | 68 |
| 1 from 15 | 6 | 0.35 | 51 |

The second row in this table gives the pharmacokinetic parameters for Example 1, as obtained after peroral administration of the prodrug compound from Example 15 (1 mg/kg of crystalline substance as a tylose suspension in water). The prodrug compound itself was not detectable at any of the times examined in the plasma of the rats.

The compound 5-[5-methyl-1-(4-methylbenzyl)-1H-pyrazol-3-yl]-3-[4-(trifluoromethoxy)phenyl]-1,2,4-oxadiazole, described as Example 1 in WO 2008/141731-A2, which, unlike the inventive compounds, does not have a heterocyclyl substituent on the benzyl head group, exhibits the following data for this parameter after peroral administration in rats: $t_{1/2}$=29 h, $AUC_{norm}$=1.9 kg·h/l, F=74%.

D. Determination of the Stability Characteristics

The stability of the inventive prodrug compounds with respect to nonspecific hydrolysis and in plasma can be determined in the tests described below:

D-1. Determination of pH-Dependent Hydrolysis Stability:

0.3 mg of the test substance (prodrug) was weighed into a 2 ml HPLC vial, and 0.6 ml of acetonitrile or acetonitrile/DMSO mixture (with up to 20 percent by volume of DMSO) was added. To dissolve the substance, the sample vessel was placed into an ultrasound bath for approx. 10 seconds. Subsequently, 1.0 ml of the particular aqueous buffer solution was added (commercially available buffer solutions of pH 2, 4, 6.5, 8 and 10) and the sample was treated again in the ultrasound bath. Over a period of 24 hours at 37° C., 5 µl of the sample solution were analysed by HPLC every hour for its content of unchanged prodrug or active ingredient released therefrom by hydrolysis. Quantification was effected via the area percentages of the corresponding HPLC peaks.

The stability values at pH 6.5 are listed below for Working Example 15:

| Time [h] | % Example 15 prodrug | % Example 1 active ingredient |
|---|---|---|
| 0 | 94 | 3 |
| 2 | 91 | 7 |
| 4 | 87 | 10 |
| 6 | 84 | 13 |
| 12 | 73 | 22 |
| 24 | 56 | 35 |

As a function of pH, the following values were obtained for Working Example 15 after 12 h:

| pH | % Example 15 prodrug | % Example 1 active ingredient |
|---|---|---|
| 2 | 89 | 6 |
| 4 | 89 | 9 |
| 6.5 | 73 | 22 |
| 8 | 64 | 30 |
| 10 | 0 | 78 |

D-2. Determination of Plasma Stability in Vitro:

1 mg of the test substance (prodrug) was weighed into a 2 ml HPLC vial, and 1.5 ml of DMSO and 1 ml of water were added. To dissolve the substance, the sample vessel was placed into an ultrasound bath for approx. 10 seconds. 0.5 ml of rat plasma or human plasma at 37° C. was added to 0.5 ml of this solution. The sample was agitated and approx. 10 μl were taken for a first analysis (time $t_0$). Within the period up to 2 hours after commencement of incubation, 4-6 further aliquots were taken for quantification. The sample was kept at 37° C. over the test period. Characterization and quantification were effected by HPLC.

The stability values in rat plasma are listed below for Working Example 15:

| Time [h] | % Example 15 prodrug | % Example 1 active ingredient |
|---|---|---|
| 0 | 95 | 5 |
| 0.5 | 87 | 11 |
| 1 | 80 | 14 |
| 1.5 | 72 | 19 |
| 2 | 69 | 20 |
| 4 | 52 | 32 |

In human plasma, the following values were obtained for Working Example 15:

| Time [h] | % Example 15 prodrug | % Example 1 active ingredient |
|---|---|---|
| 0 | 97 | 3 |
| 0.5 | 96 | 6 |
| 1 | 93 | 7 |
| 1.5 | 91 | 9 |
| 2 | 89 | 11 |
| 4 | 81 | 18 |

E. Working Examples of Pharmaceutical Compositions

The inventive compounds can be converted to pharmaceutical formulations as follows:

Tablet:

Composition:

100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of inventive compound, lactose and starch is granulated with a 5% solution (w/w) of the PVP in water. After drying, the granules are mixed with the magnesium stearate for 5 minutes. This mixture is pressed with a conventional tableting press (for tablet format see above). The guide value used for the pressing is a pressing force of 15 kN.

Suspension for Oral Administration:

Composition:

1000 mg of the inventive compound, 1000 mg of ethanol (96%), 400 mg of Rhodigel® (xanthan gum from FMC, Pennsylvania, USA) and 99 g of water.

A single dose of 100 mg of the inventive compound corresponds to 10 ml of oral suspension.

Production:

The Rhodigel is suspended in ethanol and the inventive compound is added to the suspension. The water is added while stirring. The mixture is stirred for approx. 6 h until swelling of the Rhodigel has ended.

Solution for Oral Administration:

Composition:

500 mg of the inventive compound, 2.5 g of polysorbate and 97 g of polyethylene glycol 400. A single dose of 100 mg of the inventive compound corresponds to 20 g of oral solution.

Production:

The inventive compound is suspended in the mixture of polyethylene glycol and polysorbate while stirring. The stirring operation is continued until dissolution of the inventive compound is complete.

i.v. Solution:

The inventive compound is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

F. Literature

Globocan 2002 Report
IARC International Agency for Research on Cancer: *Globocan* 2002, http://www-dep.iarc.fr/globocan/downloads.htm American Cancer Society, Cancer Facts and Figures 2005
American Cancer Society: *Cancer Facts and Figures* 2007, http://www.cancer.org/docroot/STT/content/STT_1x_Cancer_Facts_Figures_2007.asp Gibbs J B, 2000
Gibbs J B: Mechanism-based target identification and drug discovery in cancer research, *Science* 2000, 287 (5460), 1969-1973.

Semenza and Wang, 1992
Semenza G L, Wang G L: A nuclear factor induced by hypoxia via de novo protein synthesis binds to the human erythropoietin gene enhancer at a site required for transcriptional activation, *Mol. Cell. Biol.* 1992, 12 (12), 5447-5454.

Wang and Semenza, 1995
Wang G L, Semenza G L: Purification and characterization of hypoxia-inducible factor 1, *J. Biol. Chem.* 1995, 270 (3), 1230-1237.

Wang, Jiang et al., 1995
Wang G L, Jiang B H, Rue E A, Semenza G L: Hypoxia-inducible factor 1 is a basic-helix-loop-helix-PAS heterodimer regulated by cellular $O_2$ tension, *PNAS* 1995, 92 (12), 5510-5514.

Jiang, Rue et al., 1996
Jiang B H, Rue E, Wang G L, Roe R, Semenza G L: Dimerization, DNA binding, and transactivation properties of hypoxia-inducible factor 1, *J. Biol. Chem.* 1996, 271 (30), 17771-17778.

Makino, Cao et al., 2001
Makino Y, Cao R, Svensson K, Bertilsson G, Asman M, Tanaka H, Cao Y, Poellinger L: *Nature* 2001, 414 (6863), 550-554.

Jiang, Semenza et al., 1996
Jiang B H, Semenza G L, Bauer C, Marti H H: Hypoxia-inducible factor 1 levels vary exponentially over a physiologically relevant range of $O_2$ tension, *Am. J. Physiol.* 1996, 271, 1172-1180.

Maxwell, Wiesener et al., 1999
Maxwell P H, Wiesener M S, Chang G W, Clifford S C, Vaux E C, Cockman M E, Wykoff C C, Ratcliffe P J: The tumour suppressor protein VHL targets hypoxia-inducible factors for oxygen-dependent proteolysis, *Nature* 1999, 399 (6733), 271-275.

Hirota and Semenza, 2006
Hirota K, Semenza G L: Regulation of angiogenesis by hypoxia-inducible factor 1, *Crit. Rev. Oncol. Hematol.* 2006, 59 (1), 15-26.

Chen, Zhao et al., 2003
Chen J, Zhao S, Nakada K, Kuge Y, Tamaki N, Okada F, Wang J, Shindo M, Higashino F, Takeda K, Asaka M, Katoh H, Sugiyama T, Hosokawa M, Kobayashi M: Dominant-negative hypoxia-inducible factor-1 alpha reduces tumorigenicity of pancreatic cancer cells through the suppression of glucose metabolism, *Am. J. Pathol.* 2003, 162 (4), 1283-1291.

Stoeltzing, McCarty et al., 2004
Stoeltzing O, McCarty M F, Wey J S, Fan F, Liu W, Belcheva A, Bucana C D, Semenza G L, Ellis L M: Role of hypoxia-inducible factor-1alpha in gastric cancer cell growth, angiogenesis, and vessel maturation, *J. Natl. Cancer Inst.* 2004, 96 (12), 946-956.

Li, Lin et al., 2005
Li L, Lin X, Stayer M, Shoemaker A, Semizarov D, Fesik S W, Shen Y: Evaluating hypoxia-inducible factor-1 alpha as a cancer therapeutic target via inducible RNA interference in vivo, *Cancer Res.* 2005, 65 (16), 7249-7258.

Mizukami, Jo et al., 2005
Mizukami Y, Jo W S, Duerr E M, Gala M, Li J, Zhang X, Zimmer M A, Iliopoulos O, Zukerberg L R, Kohgo Y, Lynch M P, Rueda B R, Chung D C: Induction of interleukin-8 preserves the angiogenic response in HIF-1alpha-deficient colon cancer cells, *Nat. Med.* 2005, 11 (9), 992-997.

Li, Shi et al., 2006
Li J, Shi M, Cao Y, Yuan W, Pang T, Li B, Sun Z, Chen L, Zhao R C: Knockdown of hypoxia-inducible factor-1 alpha in breast carcinoma MCF-7 cells results in reduced tumor growth and increased sensitivity to methotrexate, *Biochem. Biophys. Res. Commun.* 2006, 342, 1341-1351.

Semenza, 2007
Semenza G L: *Drug Discov. Today* 2007, 12 (19-20), 853-859.

Weidemann and Johnson, 2008
Weidemann A, Johnson R S: *Cell Death and Differentiation* 2008, 15, 621-627.

Aiello et al., 1994
Aiello et al.: *New Engl. J. Med.* 1994, 331, 1480.

Peer et al., 1995
Peer et al.: *Lab. Invest.* 1995, 72, 638.

Lopez et al., 1996
Lopez et al.: *Invest. Ophthalmol. Vis. Sci.* 1996, 37, 855.

Warburg, 1956
Warburg O: *Science* 1956, 123 (3191), 309-314.

The invention claimed is:
1. A compound of the formula (I)

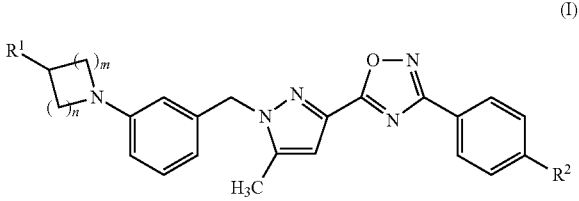

in which
m is 1 or 2,
n is 1, 2 or 3,
$R^1$ is hydroxyl or cyano,
and
$R^2$ is trifluoromethoxy, trifluoromethylsulphanyl, trifluoromethylsulphonyl, pentafluorosulphanyl or a group of the formula

in which
* denotes the bonding site to the phenyl ring,
$R^{3A}$ and $R^{3B}$ are each independently fluorine or methyl or
are joined to one another and, together with the carbon atom to which they are bonded, form a cyclopropane-1,1-diyl, cyclobutane-1,1-diyl, cyclopentane-1,1- diyl, cyclohexane-1,1-diyl, oxetane-3,3-diyl or tetrahydro-2H-pyran-4,4-diyl ring and R⁴ is hydrogen, fluorine, methyl, trifluoromethyl or methoxy, and the physiologically acceptable salts thereof.

2. The compound of the formula (I) according to claim 1, in which m and n are each independently 1 or 2, R¹ is hydroxyl or cyano, and R² is trifluoromethyl, trifluoromethoxy, trifluoromethylsulphanyl or a group of the formula

in which
* denotes the bonding site to the phenyl ring,

R³ᴬ and R³ᴮ are both methyl or are joined to one another and, together with the carbon atom to which they are bonded, form a cyclopropane-1,1-diyl, cyclobutane-1,1-diyl, oxetane-3,3-diyl or tetrahydro-2H-pyran-4,4-diyl ring and R⁴ is hydrogen, fluorine, methyl or trifluoromethyl, and the physiologically acceptable salts thereof.

3. The compound of the formula (I) according to claim 1, in which m and n are both 1 or 2, R¹ is hydroxyl or cyano, and R² is trifluoromethoxy or a group of the formula

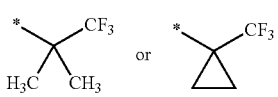

in which
* denotes the bonding site to the phenyl ring, and the physiologically acceptable salts thereof.

4. The compound of the formula (I) according to claim 1, in which

R¹ is hydroxyl, and m, n and R² are each as defined in claim 1, and the physiologically acceptable salts thereof.

5. A compound of the formula (I-PD)

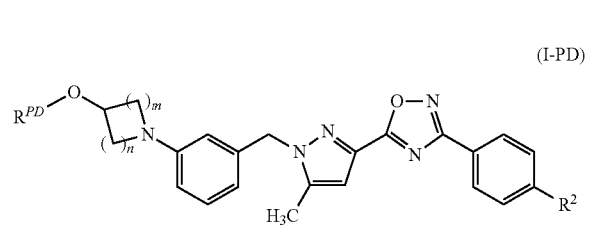

in which m, n and R² are each as defined in claim 1 and

R^PD is a prodrug group of the formula

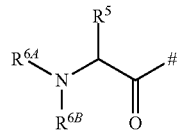

in which
# denotes the bonding site to the oxygen atom,

R⁵ is hydrogen or (C₁-C₄)-alkyl, and

R⁶ᴬ and R⁶ᴮ are each independently hydrogen or methyl, and the physiologically acceptable salts thereof.

6. The compound of the formula (I-PD) according to claim 5, in which

R^PD is a prodrug group of the formula

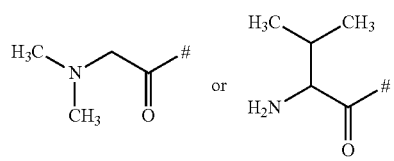

in which
# denotes the bonding site to the oxygen atom, and the physiologically acceptable salts thereof.

7. A process for preparing a compound of formula (I) as defined in claim 1, characterized in that a compound of formula (II)

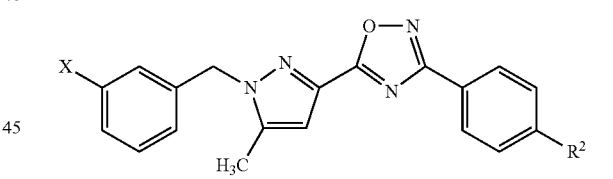

in which R² is as defined in claim 1 and

X is bromine or iodine, in the presence of a suitable palladium catalyst and of a base, is coupled with a compound of formula (III)

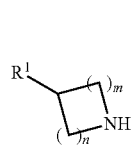

in which m, n and R¹ are each as defined in claim 1, and the resulting compound of formula (I) is optionally separated into the enantiomers and/or diastereomers thereof and/or converted using the appropriate (i) solvents and/or (ii) acids to a physiologically acceptable salt thereof.

8. A process for preparing a compound of formula (I-PD) as defined in claim 5, characterized in that a compound of formula (I-A)

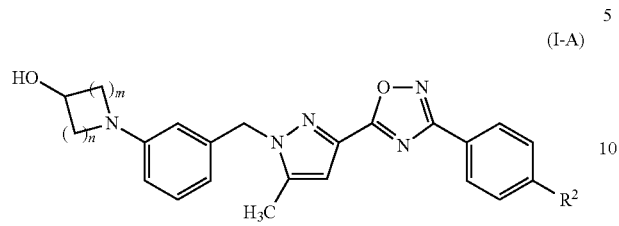

(I-A)

in which m, n and $R^2$ are each as defined in claim 5 is esterified by customary methods with a compound of the formula (VIII)

(VIII)

or an activated form thereof in which $R^{PD}$ is as defined in claim 5, and the resulting compound of formula (I-PD) is optionally separated into the enantiomers and/or diastereomers thereof and/or converted using the appropriate (i) solvents and/or (ii) acids to a physiologically acceptable salt thereof.

9. A pharmaceutical composition comprising a compound as defined in claim 1 in combination with one or more inert, nontoxic, pharmaceutically suitable excipients.

* * * * *